US006358515B2

(12) United States Patent
Ogata et al.

(10) Patent No.: US 6,358,515 B2
(45) Date of Patent: *Mar. 19, 2002

(54) HYDROQUINONE DERIVATIVES

(75) Inventors: Kazumi Ogata, Toyonaka; Hidetoshi Nakao, Itami; Kazuhiko Ito, Amagasaki; Takahiro Sakaue, Itami; Sachiko Inoue, Akashi; Masahito Iemura, Kyoto, all of (JP)

(73) Assignee: Senju Pharmaceutical Co., Ltd. (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/355,553

(22) PCT Filed: Jan. 26, 1998

(86) PCT No.: PCT/JP98/00325

§ 371 Date: Jul. 30, 1999

§ 102(e) Date: Jul. 30, 1999

(87) PCT Pub. No.: WO98/33771

PCT Pub. Date: Aug. 6, 1998

(30) Foreign Application Priority Data

Jan. 30, 1997 (JP) .............................. 9-016074
Dec. 12, 1997 (JP) .............................. 9-343028

(51) Int. Cl.$^7$ ........................ A61K 7/00; A61K 31/496; C07D 295/088; C07D 401/04; C07D 403/04
(52) U.S. Cl. .................. 424/401; 426/545; 514/252.14; 514/253.01; 514/253.12; 514/255.03; 544/295; 544/360; 544/394
(58) Field of Search ................. 514/252, 255, 514/252.14, 253.12, 253.01, 255.03; 544/295, 360, 394; 424/401; 426/545

(56) References Cited

U.S. PATENT DOCUMENTS

| | | | |
|---|---|---|---|
| 3,997,666 A | | 12/1976 | Witte et al. |
| 4,335,126 A | * | 6/1982 | Kleeman et al. ............ 424/250 |
| 4,428,950 A | | 1/1984 | Franke et al. |
| 4,616,017 A | * | 10/1986 | Baldwin et al. ............ 514/252 |
| 5,037,828 A | * | 8/1991 | Sponer et al. .............. 514/255 |
| 5,504,087 A | * | 4/1996 | Ogata et al. ............... 514/253 |

FOREIGN PATENT DOCUMENTS

| | | | |
|---|---|---|---|
| CA | 2172183 | | 9/1996 |
| DE | 2300543 | * | 7/1973 |
| EP | 0 401 652 | | 12/1990 |
| EP | 0 611 748 | | 8/1994 |
| EP | 0 735 030 | | 10/1996 |
| FR | 2488892 | * | 3/1978 |
| GB | 1451180 | | 9/1976 |
| JP | 52-83479 | | 7/1977 |
| JP | 57-139067 | | 8/1982 |
| JP | 58-22478 | | 9/1983 |
| JP | 7-157455 | | 6/1995 |
| JP | 8-325241 | | 10/1996 |

OTHER PUBLICATIONS

Kutscher et al., Synthese von potentiellen Naftopidil–Metaboliten, Arch. Pharm. 326(10), pp.803–806, 1993.*

Engel et al., Chemistry and Pharmacology of the Non–Benzodiazepine Anxiolytic Enciprazine and Related Compounds, J. Med. Chem. 33(4), pp. 2976–2981, 1990.*

Rastogi et al. Agents Acting on the Ventral Nervous System. 14 1–(p–Alkanoylphenoxy)–3–(N–arylpiperazinyl)prpan–2–ols. A New Class of Antidepressants, J. Med. Chem. 15(3), pp. 286–291, 1993.*

"Protective Groups in Organic Chemistry" by J.F.W.McOmie, pp. 171–172, 1973.*

(List continued on next page.)

Primary Examiner—Emily Bernhardt
(74) Attorney, Agent, or Firm—Millen, White, Zelano & Branigan, P.C.

(57) ABSTRACT

A hydroquinone compound is represented by the following formula (I)

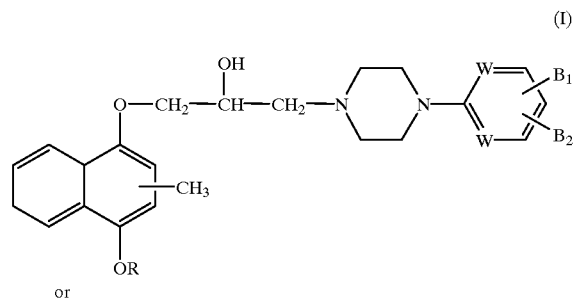

or (II)

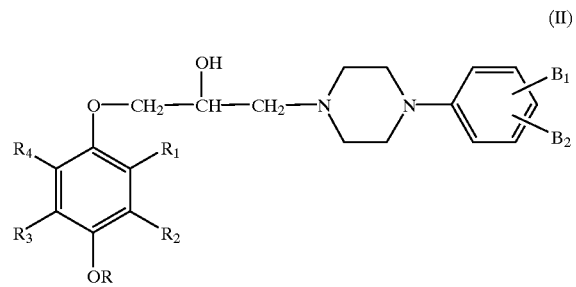

or a pharmacologically acceptable salt thereof with W, R, $R_{1-4}$, and $B_{1-2}$ defined herein.

36 Claims, 2 Drawing Sheets

OTHER PUBLICATIONS

Scatina, J. et al: "Metabolic disposition of enciprazine, a non–benxodiazepine anxiolytic drug in rat, dog and man" Xenobiotica (1991), 21(12), 1591–604 . . . see p. 1602 fig. 7.

Kutscher, Bernhard et al.: "Synthesis of potential naftopidil metabolites" Arch. Pharm. (Weinheim, Ger.) (1993) 326(10), 803–6, 1993 see especially compound 3 and *the whole document*.

Tmej, Claudia et al: "A combined Hansch/Free–Wilson approach as predictive tool in QSAR studies on propafenone–type modulators of multidrug resistance" Arch. Phar. (Weinheim, Ger.) (1998) 331(7–8), 233–240, 1998 see compound no 214627–76–6, 1–pperazineethanol, 4–(4FPhenyl)–alpha–'(4–OHphenoxy) methyl.

Niebch, G.; Locher, M.; Peter, G.; Borbe, H. O.; "Metabolic Fate of the Novel Antihypertensive Drug Naftopidil Arzneim.", FORSCH/DRUG RES., vol. 41, No. 10 (1991), pp. 1027–1032.

Grundke, M.; Himmel, H. M.; Wetter, E.; Borbe, H. O.; Raven, U.; "Characterization of Ca2+–Antagonistic Effects of Three Metabolites of the New Antihypertensive Agent Naftopidil, (Napthyl) Hydroxy–Naftopidil, (Phenyl) Hydroxy–Naftopidil, and O–desmethyl–Naftopidil." J. CARDIOVASC. PHARMACOLOGY, vol. 18, No. 6 (1991), pp. 918–925.

* cited by examiner

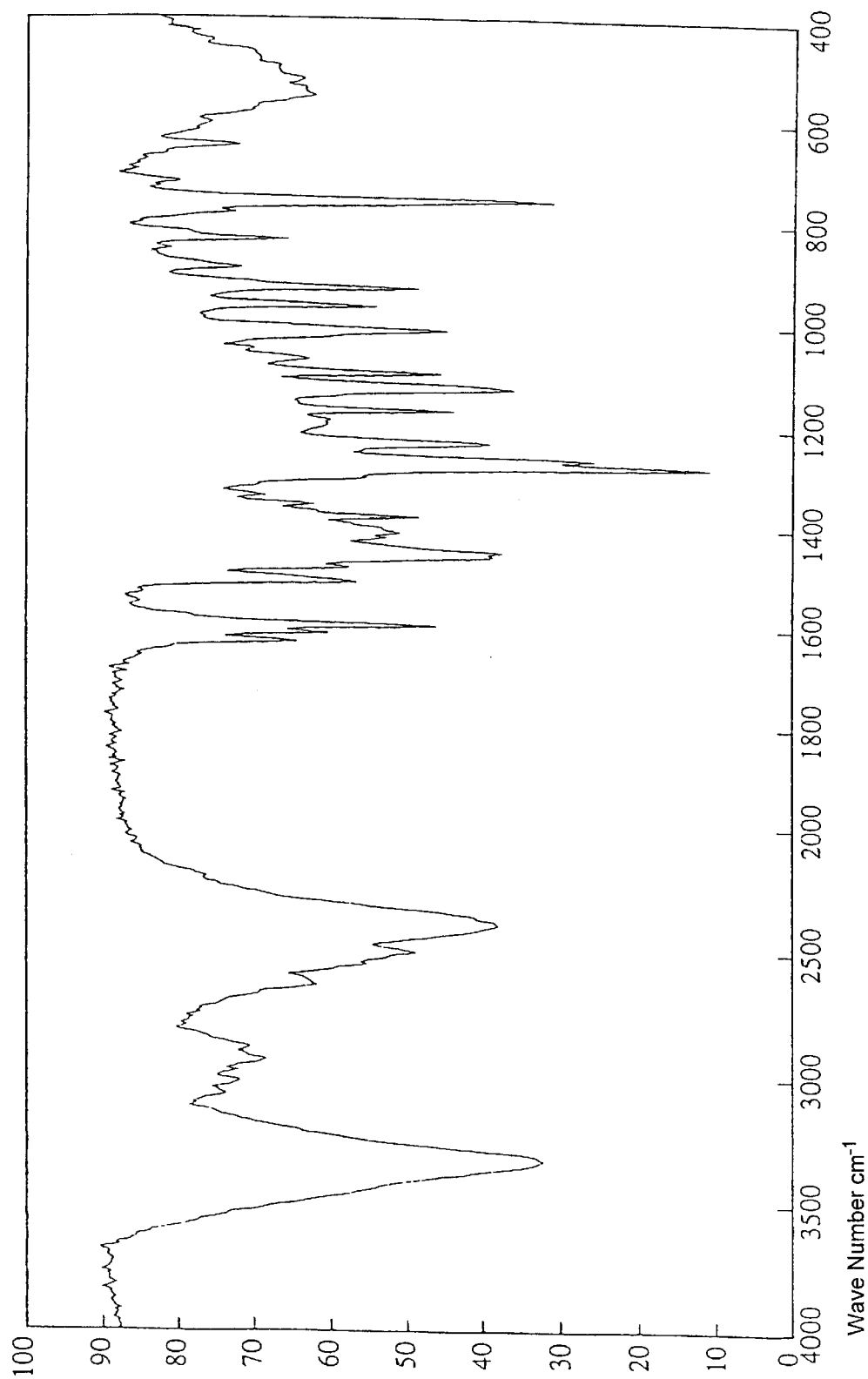

HYDROQUINONE DERIVATIVES

TECHNICAL FIELD

The present invention relates to a novel and useful hydroquinone derivative and intraocular pressure lowering, antihypertensive and radical scavenging compositions containing thereof as an active ingredient.

BACKGROUND ART

Previously the present inventors successfully synthesized certain novel propanol derivatives and found that those compounds are useful as antihypertensive as well as antiglaucomatous agents (Unexamined Japanese Patent Publication H7-157455). An antihypertensive agent and a dysuria treating agent in prostatic hypertrophy have also been known both of which contain a naphthol derivative, 1-phenyl-4-[3-(naphth-1-yl-oxy)-2-hydroxy-propyl] piperazine, as an active ingredient, [Unexamined Japanese Patent Publication H3-31271]. Furthermore, certain benzylalcohol derivatives have been disclosed which have an α1-adrenergic receptor blocking activity with less side effect of orthostatic hypotension, and which are useful for glaucoma and ocular hypertension [Unexamined Japanese Patent Publication H9-12563].

DISCLOSURE OF THE INVENTION

The present inventors have further investigated relating compounds to the above and their pharmacological effects, and, as a result, have successfully synthesized a group of novel hydroquinone derivatives and found that they have potent intraocular pressure lowering, antihypertensive and radical scavenging activities. The present invention has been made on the basis of these findings and through further investigation.

Thus, the present invention relates to: (1) A hydroquinone derivative represented by the following formula:

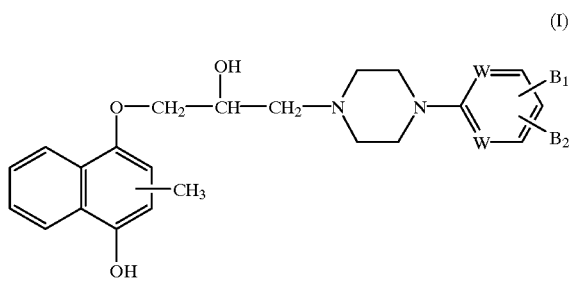

(I)

or

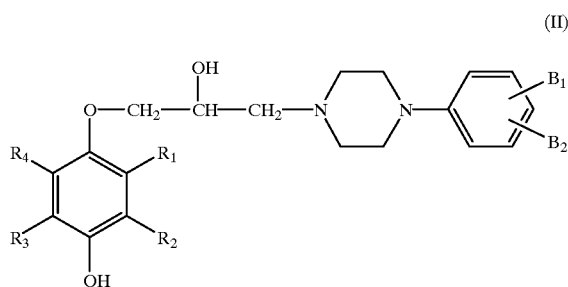

(II)

wherein $B_1$ and $B_2$ in formula (I) are the same or different and at any position on the benzene ring (when W is nitrogen, however, at any other position on the benzene ring) and each denotes a substituent selected from the group consisting of hydrogen, halogen, hydroxyl, lower alkoxyl and carboxyl, and the substituent $CH_3$ is at position 2 or 3, and W are the same or different and each denotes a nitrogen or carbon atom. $R_1$, $R_2$, $R_3$ and $R_4$ in formula (II) are the same or different and each denotes a substituent selected from the group consisting of hydrogen, lower alkyl and lower alkoxyl, and $B_1$ and $B_2$ are as hereinbefore defined, or a pharmacologically acceptable salt thereof (hereinafter referred to as "the present compound"), and (2) intraocular pressure lowering, antihypertensive and radical scavenging compositions containing thereof

BRIEF DESCRIPTION OF THE DRAWINGS

FIG. 2 illustrates an infra-red absorption spectrum (IR) of the compound synthesized in Example 4.

DETAILED DESCRIPTION OF THE INVENTION

Figure 1:
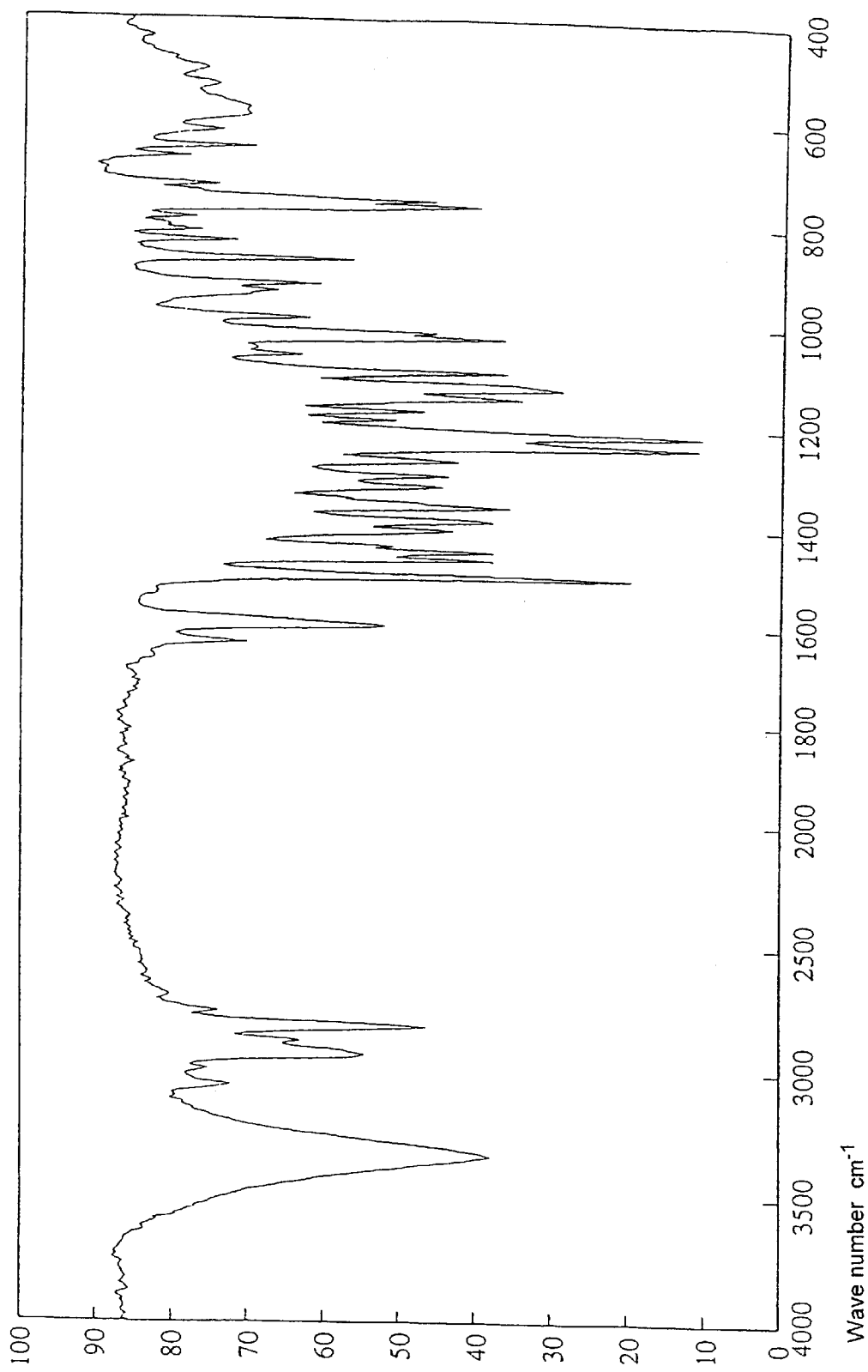
FIG. 1 illustrates an infra-red absorption spectrum (IR) of the compound synthesized in Example 2.

The halogen for $B_1$ and $B_2$ in formulas (I) and (II) above includes F, Cl, Br and I.

The lower alkyl for $R_1$, $R_2$, $R_3$ and $R_4$ in formula (II) above is linear, branched or cyclic and preferably comprises 1–5 carbon atoms. Examples include methyl, ethyl, n-propyl, isopropyl, cyclopropyl, n-butyl, tert-butyl, sec-butyl, n-pentyl, 1-ethylpropyl and isopentyl.

The lower alkoxyl for $R_1$, $R_2$, $R_3$ and $R_4$ and $B_1$ and $B_2$ in formulas (I) and (II) above preferably comprises 1–3 carbon atoms. Examples include methoxyl, ethoxyl, propoxyl or isopropoxyl.

For the purpose of the present invention, the present compound represented by formula (I) or (II) above can be used either in their free form or in the form of a pharmacologically acceptable salt thereof. Examples of such salts include inorganic acid salts such as hydrochloride, sulfate and nitrate as well as organic acid salts such as maleate and tartrate. Other salts also may be used insofar as they are pharmacologically acceptable.

The one of the present compound represented by formula (I) can be synthesized in accordance, for example, with the following synthetic scheme or analogously thereto:

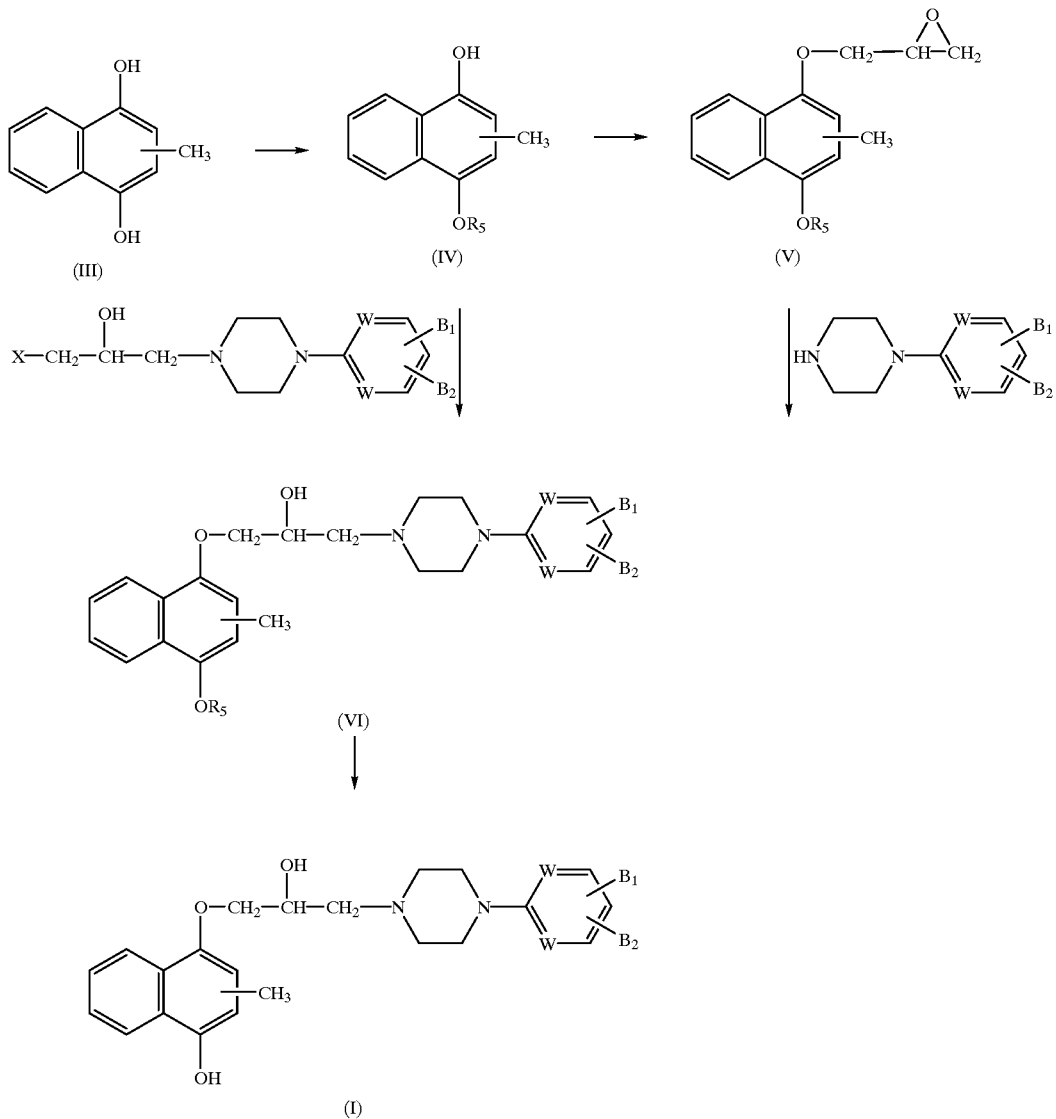

(In the reaction scheme above, $R_5$ denotes acyl or benzyl, X denotes halogen, and $R_1$, $R_2$, $R_3$, $R_4$, $B_1$, $B_2$ and W are as hereinbefore defined. Also in the reaction scheme above, the substituent $CH_3$ is at position 2 or 3.)

The acyl for $R_5$ in the reaction scheme above includes, for example, acetyl and benzoyl. The halogen for X includes F, Cl, Br and I.

First, vitamin $K_3$ is reduced with a suitable reducing agent (e.g., zinc and hydrochloric acid) to form 1,4-dihydroxy-2-methylnaphthalene (III), which then is mono-acylated with an acylation reagent (e.g., benzoyl chloride) in the presence of a deacidification agent (e.g., pyridine), and, optionally, further benzylated with a benzylation reagent (e.g., benzyl bromide) and treated with an acid or a base (deacylation). Position 4 has thus undergone O-acylation or O-benzylation, providing 4-O-acyl-2-methylnaphthol or 4-O-benzyl-3-methylnaphthol (IV). Then, this is reacted with epichlorohydrin (chloromethyloxirane) in the presence of a deacidification agent to form 4-acyloxy-2-methyl-1-(2,3-epoxypropane)naphthol or 4-benzyloxy-3-methyl-1-(2,3-epoxypropane)naphthol (V), which in turn is reacted with a pyridylpiperazine, a pyrimidylpiperazine or a $B_1B_2$-substituted phenylpiperazine to form 1-(2-methyl-4-acyloxynaphthoxy)-3-[4-(2-pyridyl)-1-piperazinyl]-propan-2-ol, 1-(2-methyl-4-acyloxynaphthoxy)-3-[4-(2,6-pyrimidyl)-1-piperazinyl]propan-2-ol, or 1-(2-methyl-4-acyloxynaphthoxy)-3-[4-($B_1B_2$-substituted phenyl)-1-piperazinyl]propan-2-ol or 1-(3-methyl-4-benzyloxynaphthoxy)-3-[4-(substitute moiety respectively corresponding to those aforementioned)-1-piperazinyl] propan-2-ol (VI), the protecting acyl or benzyl group at position 4 of which then is cleaved with a base or by catalytic reduction to give the present compound (I).

Alternatively, compound (IV) is reacted with 1-halogenated-3-[4-($B_1B_2$-substituted phenyl)-1-piperazinyl]propan-2-ol in the presence of a deacidification agent to from compound (VI), the benzyl of which is cleaved by catalytic reduction to give the present compound (I).

The other of the present compound represented by formula (II) can be synthesized in accordance, for example, with the following synthetic scheme or analogously thereto:

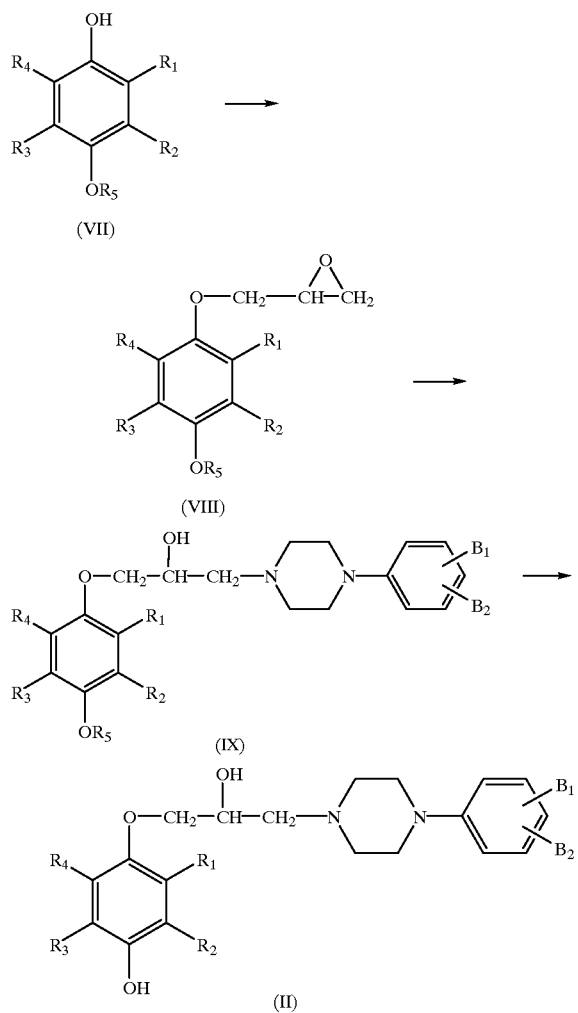

(In the reaction scheme, $R_1$, $R_2$, $R_3$, $R_4$, $R_5$, $B_1$ and $B_2$ are as hereinbefore defined.)

The starting material, mono-acylated or mono-benzylated hydroquinone derivative (VII) can be synthesized by a known method. For example, 2,3-dimethylhydroquinone monoacetate and 2,5-dimethylhydroquinone monoacetate can be synthesized by a method described in Bioorg. Chem. (1971), 1(4), pp. 345–60, or analogously thereto. And, 2,3,5-trimethylhydroquinone-4-acetoxyphenol can be synthesized by a method described in Czechoslovak Patent Nos. 8405551 or 7601867, or analogously thereto.

Then, this is reacted with chloromethyloxirane in the presence of a deacidification agent, e.g. potassium carbonate, in acetone, methyl ethyl ketone or acetonitrile to form (2,3-epoxy)glycidylhydroquinone derivative (VIII). 1-(2,3,5-trimethyl-4-acetoxyphenoxy)-2,3-epoxypropane, in particular, can be synthesized by a method described in Czechoslovak Patent No.7704666. Then this is subjected to addition reaction with a phenylpiperazine derivative in heated alcohol or dioxane to form compound (XI), the protecting acyl or benzyl group of which then is cleaved with a base or by catalytic reduction to give the present compound, a hydroquinone derivative (II).

The present compound (I) or (II) thus obtained may be converted into one of pharmacologically acceptable salts in a conventional manner. For example, the present compound thus obtained is treated with either an inorganic acid such as hydrochoric acid or sulfuric acid or with an organic acid such as maleic acid or tartaric acid, thereby giving respective salts. Conversion to a salt may be carried out either after isolation of the present compound from the reaction mixture or without isolation from the reaction mixture.

The present compound (I) or (II) obtained as above is a novel compound, which has so far not been found in literatures, and is useful as an antihypertensive, intraocular pressure lowering and radical scavenging agent.

As the present compound (I) or (II) has a radical scavenging activity, it can be used as an agent for prevention and treatment of a variety of diseases such as ischemic disorders of organs (e.g., myocardial infarction, heart failure, arrhythmia, cerebral infarction, cerebral apoplexy, renal failure, etc.) and cataract, and as a senility preventive agent. The present compound is also expected to be useful as an agent for prevention and treatment of climacteric disturbances and as an anti-inflammatory agent. Furthermore, the present compound can be incorporated into cosmetic compositions and foodstuffs.

The pharmaceutical compositions of the present invention may contain one or more species of the present compound (I) or (II) in combination in accordance with aim and necessity.

The pharmaceutical compositions of the present invention can be administered either orally or parenterally as an antihypertensive, intraocular pressure lowering or radical scavenging medicine. As for their dosage forms, they may be prepared in any of such forms as solid forms like tablets, granules, powder, capsules or liquid forms like injection and eye drops, by conventional methods. Such preparations may contain usual additives such as excipients, binders, thickeners, dispersing agents, resorption enhancers, buffering agents, surfactants, solubilizer, preservatives, emulsifiers, isotonizers, stabilizers and pH adjusting agents.

The dose of the present compound (I) or (II) when used as a medicine, although dependent on the species of the present compound employed, body weight and age of the patient, the disease to be treated, its condition and the manner of administration, is preferably, for example, about 1 mg to about 30 mg once a day for an adult in the case of injections, and about 1 mg to about 100 mg at a time and several times a day for an adult in the case of oral preparations. In the case of eye drops, it is preferable to administer an eye drops of about 0.01–5 (w/v) %, a few drops at a time and several times a day for an adult.

When employing the present compound (I) or (II) in cosmetic compositions, it can be incorporated into creams, lotions, toilet waters, etc., aiming at ultraviolet light absorption or a skin beautifying effect, or for stabilization of other ingredients in the cosmetic compositions. Usual ingredients for cosmetics may be employed in cosmetic compositions with the incorporated present compound.

When employed in cosmetic compositions, although dependent on the species of the compound and the type of the intended cosmetic composition and the aim of incorporation, the present compound (I) or (II) is incorporated, in general, preferably at about 0.001–5 (w/w) %, more preferably about 0.005–2 (w/w) %.

In addition, when added to foodstuffs as an antioxidant, although dependent on the species of the compound and the type of the intended foodstuff, the present compound (I) or (II) is incorporated, in general, preferably at about 0.001–5 (w/w) %, more preferably about 0.005–0.2 (w/w) %.

The compositions of the present invention may include other antihypertensive, intraocular pressure lowering and radical scavenging agents and/or other ingredients of different pharmacological activities, insofar as they are not contradictory to the purpose of the present invention.

BEST MODE FOR CARRYING OUT THE INVENTION

The present invention is described in further detail below by means of reference examples and working examples.

Reference Example

4-Benzoyloxy-2-methylnaphthol 9.7 g (0.056 mol) of 2-methyl-1,4-dihydroxynaphthalene was dissolved in 60 ml of pyridine, and, while stirring under ice-cooling, 8.4 g (0.06 mol) of benzoyl chloride was added dropwise. Following completion of the addition, stirring was continued under ice-cooling for 30 minutes, and for further one hour at room temperature. The reaction mixture was concentrated under reduced pressure, the residual oil extracted with ethyl acetate, washed with 1N HCl and then water, and the organic layer concentrated under reduced pressure. Methanol was added to the residue, the precipitated crystals collected by filtration and recrystallized from methanol to give 10.8 g of white crystals, m.p. 172–174° C.

1-Benzyloxy-2-methyl-4-benzoyloxynaphthalene 10.8 g (0.039 mol) of 4-benzoyloxy-2-methylnaphthol was dissolved in 100 ml of acetone, and to this was added 5.5 g (0.04 mol) of anhydrous potassium carbonate, and, while stirring at room temperature, 7.7 g (0.045 mol) of benzyl bromide was added dropwise over 30 minutes, and following completion of the addition, stirring was continued for 20 hours at room temperature. Then, inorganic salt was filtered out and the filtrate was concentrated under reduced pressure. The residue was extracted with ethyl acetate, washed with water, and the solvent evaporated under reduced pressure. n-Hexane was added to the residue to cause crystallization. Recrystallization from ethyl acetate-n-hexane gave 11.9 g of white crystals, m.p. 179–180° C.

4-Benzyloxy-3-methylnaphthol 11.9 g (0.032 mol) of 1-benzyloxy-2-methyl-4-benzoyloxynaphthalene was suspended in 120 ml of methanol, and to this was added 20 ml of 2N NaOH, followed by stirring for 2 hours at room temperature. After evaporation of methanol from the reaction mixture under reduced pressure, the residue was acidified with hydrochloric acid, and extracted with ethyl acetate. The organic layer was washed with a sodium hydrogen carbonate aqueous solution and then with water, and ethyl acetate evaporated under reduced pressure. The residue was dissolved in methanol, decolorized with activated carbon, and following filtering out of the activated carbon, water was added to the filtrate, and precipitated crystals were collected, recrystallized from methanol-water to give 5.2 g of white plates, m.p. 159–161° C.

EXAMPLE 1

1-(3-Methyl-4-benzyloxynaphthoxy)-3-[4-(2-methoxyphenyl)-1-piperazinyl]propan-2-ol dihydrochloride Method A)

3.0 g (0.011 mol) of 4-benzyloxy-3-methylnaphthol was dissolved in 50 ml of acetone, and to this was added 1.5 g (0.011 mol) of anhydrous potassium carbonate. After stirring for 10 minutes at room temperature, 5.6 g (0.06 mol) of chloromethyloxirane was added, followed by a four-hour refluxing while stirring. After allowing the reaction mixture to cool down, inorganic salt was filtered out, and the filtrate concentrated under reduced pressure. The residual oil was extracted with ethyl acetate, washed with 1N HCl and then with water, and ethyl acetate evaporated under reduced pressure to give about 3 g of brown oil.

Then, this oil and 1.9 g (0.01 mol) of 1-(2-methoxyphenyl)piperazine were dissolved in 50 ml of dioxane, refluxed for 6 hours while stirring on an oil bath, and then the solvent was evaporated under reduced pressure. The residual oil was extracted with ethyl acetate, washed with 0.1 N HCl, water, a sodium hydrogen carbonate aqueous solution and then with water in the order, and the ethyl acetate layer concentrated under reduced pressure. The residue then was dissolved in ethanol and treated with activated carbon, then acidified with hydrochloric acid and, after addition of isopropyl ether, precipitated crystals were collected by filtration. The thus obtained crude crystals were recrystallized from methanol-ethyl acetate to obtain 1.8 g of white crystals, m.p. 189–191° C. (decomp.).

Elemental analysis: For $C_{32}H_{36}N_2O_4 \cdot 2HCl$ Calculated (%): C, 65.64; H, 6.54; N, 4.78; Found (%): C, 65.55; H, 6.39; N, 4.87.

Method B)

1.9 g of 1-(2-methoxyphenyl)piperazine and 3.0 g of chloromethyloxirane were dissolved in 60 ml of methanol. After 4-hour reflux with heating, the solvent was evaporated. The residual oil was extracted with ethyl acetate, washed with water. Evaporation of ethyl acetate gave about 2 g of oil. To this were added 2.3 g of 4-benzyloxy-3-methylnaphthol and 1.5 g of anhydrous potassium carbonate and after 4-hour reflux with heating in 60 ml of acetone, inorganic salt was filtered out and the filtrate concentrated. The residual oil was extracted with ethyl acetate, washed with 0.1 N HCl, 3% sodium hydrogen carbonate and then water in the order, and ethyl acetate evaporated. The residue was dissolved in ethanol and acidified with HCl. After addition of isopropyl ether, precipitated crystals were collected by filtration and recrystallized from methanol-ethyl acetate to give 1.8 g of crystals, m.p. 189–191° C.

EXAMPLE 2

1-(3-Methyl-4-hydroxynaphthoxy)-3-[4-(2-methoxyphenyl)-1-piperazinyl]propan-2-ol 1.8 g (0.003 mol) of the above crystals were dissolved in 100 ml of 80% methanol and catalytically reduced with palladium-carbon (Pd-C) under a hydrogen gas flow. After filtering out the catalyst, the reaction mixture was concentrated under reduced pressure, neutralized with sodium hydrogen carbonate, and extracted with ethyl acetate. After washing with water, the solvent was evaporated under reduced pressure. The residue was crystallized with an addition of isopropyl ether and collected by filtration. This was recrystallized from ethanol to give 0.6 g of white crystals, m.p. 198–200° C. (decomp.).

TLC: silica gel: Rf=0.90 (dioxane: 28 (w/v) % aqueous ammonia: 15 (w/v) % sodium acetate=7:2:1)

Elemental analysis: For $C_{25}H_{30}N_2O_4$ Calculated (%): C, 71.07; H, 7.16; N, 6.63; Found (%): C, 71.13; H, 7.21; N, 6.71.

EXAMPLE 3

1-(2-Methyl-4-benzoyloxynaphthoxy)-3-[4-(2-methoxyphenyl)-1-piperazinyl]propan-2-ol hydrochloride 3.7 g (0.013 mol) of 4-benzyloxy-2-methylnaphthol was dissolved in 100 ml of acetone, and to this was added 1.8 g (0.013 mol) of anhydrous potassium carbonate. After stirring 10 minutes at room temperature, 6.5 g (0.07 mol) of chloromethyloxirane was added, followed by refluxing for four hours while stirring. Inorganic salt was filtered out and the solvent evaporated under reduced pressure. The residual oil was extracted with ethyl acetate, washed with 1N HCl and then with water, and ethyl acetate evaporated under reduced pressure to give 3.3 g of residual brown oil.

The above compound and 1.9 g (0.01 mol) of 1-(2-methoxyphenyl)piperazine were dissolved in 50 ml of dioxane, refluxed for six hours while stirring, and the solvent evaporated under reduced pressure. The residual oil was extracted with ethyl acetate, washed with 1N HCl and then with water, and the solvent evaporated under reduced pressure. The residue was dissolved in ethanol, treated with activated carbon, and acidified with hydrochloric acid. After addition of isopropyl ether, precipitated crystals were collected by filtration. The thus obtained crude crystals were recrystallized from ethanol-isopropyl ether to give 2.2 g of white crystals, m.p. 219–220° C. (decomp.).

EXAMPLE 4

1-(2-Methyl-4-hydroxynaphthoxy)-3-[4-(2-methoxyphenyl)-1-piperazinyl]propan-2-ol dihydrochloride 2.2 g of the above compound was dissolved in 70 ml of methanol, and to this was added 5 ml of 2N NaOH, followed by stirring for two hours at room temperature. After neutralization with 2N HCl, the mixture was extracted with ethyl acetate, washed with water, and ethyl acetate was evaporated under reduced pressure. The residual oil was dissolved in methanol, treated with activated carbon and, after evaporation of the solvent, acidified with hydrochloric acid. After addition of isopropyl ether, precipitated crystals were collected by filtration, recrystallized from methanol-ethyl acetate to give 1.0 g of white crystals, m.p. 227–229° C. (decomp.).

TLC: silica gel: Rf=0.85 (dioxane: 28 (w/v) % aqueous ammonia: 15 (w/v) % sodium acetate=7:2:1.

Elemental analysis: For $C_{25}H_{30}N_2O_4 \cdot 2HCl$ Calculated (%): C, 60.61; H, 6.51; N, 5.65; Found (%): C, 60.32; H, 6.80; N, 5.81.

EXAMPLE 5

1-(2-Methyl-4-hydroxynaphthoxy)-3-[4-(2-methylphenyl)-1-piperazinyl]propan-2-ol hydrochloride Using 3.7 g of 4-benzyloxy-2-methylnaphthol, 1.4 g of anhydrous potassium carbonate, 5.0 g of chloromethyloxirane, 2.2 g of 1-(2-tolyl)piperazine hydrochloride and 1.2 g of triethylamine, reaction was carried out as in Examples 1-A and 2. The thus obtained crystals were recrystallized from ethanol-isopropyl ether to give 2.3 g, m.p. 261–263° C. (decomp.).

Elemental analysis: For $C_{25}H_{30}O_3N_2 \cdot HCl$ Calculated (%): C, 67.78; H, 7.05; N, 6.32; Found (%): C, 67.42; H, 7.33; N, 6.31.

EXAMPLE 6

1-(3-Methyl-4-benzyloxynaphthoxy)-3-[4-(2-fluorophenyl)-1-piperazinyl]propan-2-ol hydrochloride Using 5.3 g (0.02 mol) of 4-benzyloxy-3-methylnaphthol, 2.8 g (0.02 mol) of anhydrous potassium carbonate, 9.3 g (0.10 mol) of chloromethyloxirane, 4.3 g (0.02 mol) of 1-(2-fluorophenyl)piperazine hydrochloride and 2.0 g (0.02 mol) of triethylamine, reaction was carried out as in Example 1-A to give 6.2 g of white crystals, m.p. 218–220° C. (decomp.).

EXAMPLE 7

1-(3-Methyl-4-hydroxynaphthoxy)-3-[4-(2-fluorophenyl)-1-piperazinyl]propan-2-ol hydrochloride 6.2 g of the above crystals were subjected to catalytic reduction as in Example 2, and recrystallized from methanol-ethyl acetate to give 2.5 g of white crystals, m.p. 253–256° C. (decomp.).

Elemental analysis: For $C_{24}H_{27}FN_2O_3 \cdot HCl$ Calculated (%): C, 64.50; H, 6.31; N, 6.27; Found (%): C, 64.41; H, 6.34; N, 6.27.

EXAMPLE 8

1-(2-Methyl-4-hydroxynaphthoxy)-3-[4-(2,5-dimethoxyphenyl)-1-piperazinyl]propan-2-ol dihydrochloride Using 2.8 g (0.01 mol) of 4-benzoyloxy-2-methylnaphthol, 1.4 g (0.01 mol) of anhydrous potassium carbonate, 4.6 g (0.05 mol) of chloromethyloxirane, 2.9 g (0.01 mol) of 1-(2,4-dimethoxyphenyl)piperazine dihydrochloride and 2.2 g (0.02 mol) of triethylamine, reaction was carried out as in Examples 3 and 4 to give 0.6 g of crystals, m.p. 163–165° C. (decomp.).

Elemental analysis: For $C_{26}H_{32}N_2O_4 \cdot 2HCl$ Calculated (%): C, 59.43; H, 6.52; N, 5.33; Found (%): C, 59.48; H, 6.68; N, 5.59.

EXAMPLE 9

1-(2-Methyl-4-hydroxynaphthoxy)-3-[4-(3,4-dimethoxyphenyl)-1-piperazinyl]propan-2-ol dihydrochloricle Using 2.8 g (0.01 mol) of 4-benzoyloxy-2-methylnaphthol, 1.4 g (0.01 mol) of anhydrous potassium carbonate, 4.6 g (0.05 mol) of chloromethyloxirane, 2.9 g (0.01 mol) of 1-(3,4-dimethoxyphenyl)piperazine dihydrochloride and 2.0 g (0.02 mol) of triethylamine, reaction was carried out as in Examples 3 and 4 to give 0.4 g of white crystals, m.p. 180–182° C. (decomp.).

Elemental analysis: For $C_{26}H_{32}N_2O_5 \cdot 2HCl$ Calculated (%): C, 59.43; H, 6.52; N, 5.33; Found (%): C, 59.51; H, 6.74; N, 5.00.

EXAMPLE 10

1-(2-Methyl-4-hydroxynaphthoxy)-3-[4-(2,4-dimethoxyphenyl)-1-piperazinyl]propan-2-ol dihydrochloride Using 2.8 g (0.01 mol) of 4-benzoyloxy-2-methylnaphthol, 1.4 g (0.01 mol) of anhydrous potassium carbonate, 4.6 g (0.05 mol) of chloromethyloxirane, 2.9 g (0.01 mol) of 1-(2,4-dimethoxyphenyl)piperazine dihydrochloride and 2.0 g (0.02 mol) of triethylamine, reaction was carried out as in Examples 2 and 4 to give 0.7 g of crystals, m.p. 175–177° C. (decomp.).

Elemental analysis: For $C_{26}H_{32}N_2O_5 \cdot 2HCl$ Calculated (%): C, 59.43; H, 6.52; N, 5.33; Found (%): C, 59.48; H, 6.68; N, 5.59.

EXAMPLE 11

1-(2-Methyl-4-hydroxynaphthoxy)-3-[4-(2-hydroxyphenyl)-1-piperazinyl]propan-2-ol hydrochloride Using 3.7 g of 4-benzyloxy-2-methylnaphthol, 1.4 g of anhydrous potassium carbonate, 5.0 g of chloromethyloxirane, 2.3 g of 1-(2-hydroxyphenyl)piperazine hydrochloride and 1.2 g of triethylamine, reaction was carried out as in Examples 1-A and 2. The thus obtained crystals were recrystallized from ethanol-isopropyl ether to give 1.8 g of crystals, m.p. 267–269° C. (decomp.).

Elemental analysis: For $C_{24}H_{28}N_2O_4 \cdot HCl$ Calculated (%): C, 64.78; H, 6.57; N, 6.30; Found (%): C, 64.55; H, 6.74; N, 6.21.

EXAMPLE 12

4-Benzyloxy-2,3-dimethoxy-5-methylphenol

Using 5.05 g of 2,3-dimethoxy-5-methyl-1,4-dihydroxybenzene, 3.80 g of benzoyl chloride and 100 ml of pyridine, reaction and workup carried out as in the Reference Example gave 5.57 g of 4-benzoyloxy-2,3-dimethoxy-5-methylphenol, m.p. 109–111° C. Then, this 5.57 g was dissolved in 50 ml of DMF and added dropwise under an argon gas flow to a suspension of 0.84 g of sodium hydride in 50 ml of DMF. After the addition, stirring was continued for 30 minutes, and 2.6 ml of benzyl bromide was added dropwise and stirring continued for 2 hours at room temperature. The reaction mixture was poured into ice water, extracted with ethyl ether, washed with water, the solvent evaporated under reduced pressure, and thus obtained residue dissolved in 100 ml of methyl alcohol, and to this was added dropwise 5.10 g of sodium methylate (28% methyl alcohol solution) under ice-cooling and stirred for 12 hours at room temperature. Evaporation of the solvent under reduced pressure, neutralization with 2N HCl, extraction with ethyl ether and then evaporation of the solvent under reduced pressure gave 3.69 g of yellow oil.

EXAMPLE 13

1-(4-Benzyloxy-2,3-dimethoxy-5-methylphenoxy)-3-[4-(2-methoxyphenyl)-1-piperazinyl]propan-2-ol Then, using 3.69 g of the compound of Example 12, 1.82 g of anhydrous potassium carbonate, 1.5 ml of chloromethyloxirane and 100 ml of methyl ethyl ketone, reaction and workup carried out as in Example 1-A gave about 4.5 g of 1-(4-benzyloxy-2,3-dimethoxy-5-methylphenoxy)-2,3-epoxypropane as yellow oil. Using this epoxy compound, 3.05 g of 1-(2-methoxyphenyl)piperazine and 100 ml dioxane, reaction and workup carried out as in Example 1-A followed by purification by column chromatography (silica gel, elution with ethyl acetate:hexane=1:0.5) gave 4.61 g of yellow oil.

EXAMPLE 14

1-(2,3-Dimethoxy-4-hydroxy-5-methylphenoxy)-1-[4-(2-methoxyphenyl)-1-piperazinyl]propan-2-ol hydrochloride The 4.61 g of the compound of Example 13 above was subjected to catalytic reduction with 5% palladium-carbon in 100 ml of dioxane as in Example 2 and, after conversion to hydrochloride with 2N HCl, recrystallized from methanol-acetone to give 3.05 g of white crystals, m.p. 138–140° C.

Elemental analysis: For $C_{23}H_{32}N_2O_6 \cdot HCl \cdot 1/2H_2O$ Calculated (%): C, 57.80; H, 7.17; N, 5.86; Found (%): C, 57.77; H, 6.90; N, 6.03.

EXAMPLE 15

4-Benzyloxy-3,5-dimethylphenol

Using 4.70 g of 2,6-dimethyl-1,4-dihydroxybenzene, 4.0 ml of benzoyl chloride and 100 ml of pyridine, reaction and workup carried out as in Reference Example gave 6.35 g of 4-benzoyloxy-2,6-dimethylphenol as white crystals, m.p. 139.5–141.0° C. Using 6.35 g of the white crystals, 1.26 g of sodium hydride, 4.2 ml of benzyl bromide and 50 ml of DMF, reaction and workup carried out as in Example 12 gave 4.22 g of yellow oil.

EXAMPLE 16

1-(4-Benzyloxy-3,5-dimethylphenoxy)-3-[4-(2-methoxyphenyl)-1-piperazinyl]propan-2-ol Using 4.22 g of the compound of Example 15, 2.7 ml of chloromethyloxirane, 2.42 g of anhydrous potassium carbonate and 100 ml of methyl ethyl ketone, reaction and workup carried out as in Example 1-A gave about 4.80 g of 1-(4-benzyloxy-3,5-dimethylphenoxy)-2,3-epoxypropane as yellow oil. Using the epoxy compound thus obtained, 4.04 g of 1-(2-methoxyphenyl)piperazine and 100 ml of dioxane, reaction and workup carried out as in Example 1-A followed by purification by column chromatography (silica gel, eluted with ethyl acetate:hexane=1:1) gave 5.96 g of white crystals, m.p. 93–94° C.

Elemental analysis: For $C_{29}H_{36}N_2O_4$ Calculated (%): C, 73.08; H, 7.61; N, 5.88; Found (%): C, 72.78; H, 7.45; N, 5.76.

EXAMPLE 17

1-(3,5-Dimethyl-4-hydroxyphenoxy)-3-[4-(2-methoxyphenyl)-1-piperazinyl]propan-2-ol dihydrochloride Then, 4.22 g of the compound of Example 16 above was subjected to catalytic reduction with 5% palladium-carbon in 100 ml of dioxane as in Example 2 and, after conversion to hydrochloride with 2N HCl, recrystallized from methanol-acetone to give 3.41 of white crystals, m.p. 208–210° C. (decomp.).

Elemental analysis: For $C_{22}H_{30}N_2O_4 \cdot 2HCl$ Calculated (%): C, 57.52; H, 7.02; N, 6.10; Found (%): C, 57.54; H, 7.01; N, 6.11.

EXAMPLE 18

4-Benzyloxy-3-tert-butylphenol

Using 6.65 g of 2-tert-butyl-1,4-dihydroxybenzene, 4.6 ml of benzoyl chloride and 200 ml of pyridine, reaction and workup carried out as in Reference Example gave 9.35 g of 4-benzoyloxy-2-tert-butylphenol as white crystals, m.p. 120–121° C. Using. 9.35 g of the white crystals, 1,47 g of sodium hydride, 6.27 g of benzyl bromide and 40 ml of DMF, reaction and workup carried out as in Example 12 gave 6.07 g of yellow oil.

EXAMPLE 19

1-(4-Benzyloxy-3-tert-butylphenoxy)-3-[4-(2-methoxyphenyl)-1-piperazinyl]propan-2-ol Then, using 6.07 g of the compound of Example 18 above, 4.0 ml of chloromethyloxirane, 3.26 g of anhydrous potassium carbonate and 100 ml of methyl methyl ketone, reaction and workup carried out as in 1-A gave about 8.00 g of 1-(4-benzyloxy-3-tert-butylphenoxy)-2,3-epoxypropane as brown oil. Using the epoxy compound thus obtained, 4.82 g of 1-(2-methoxyphenyl)piperazine and 100 ml of dioxane, reaction and workup carried out as in Example 1-A followed by recrystallization from isopropyl ether gave 6.48 g of white crystals, m.p. 133–134° C.

Elemental analysis: For $C_{31}H_{40}N_2O_4$ Calculated (%): C, 73.78; H, 7.99; N, 5.55; Found (%): C, 73.49; H, 8.05; N, 5.58.

EXAMPLE 20

1-(3-tert-Butyl-4-hydroxyphenoxy)-3-[4-(2-methoxyphenyl)-1-piperazinyl]propan-2-ol hydrochloride Then, 6.48 g of the compound of Example 19 above was subjected to catalytic reduction with 5% palladium-carbon in 100 ml of dioxane as in Example 2 and, after conversion to hydrochloride with 2N HCl, recrystallized from methanol-ether to give 4.26 g of white crystals, m.p. 170–172° C.

Elemental analysis: For $C_{24}H_{34}N_2O_4 \cdot HCl \cdot 1/2H_2O$ Calculated (%): C, 62.66; H, 7.89; N, 6.09; Found (%): C, 62.33; H, 7.69; N, 5.97.

EXAMPLE 21

1-(2,5-Dimethyl-4-hydroxyphenoxy)-3-[4-(2-methoxyphenyl)-1-piperazinyl]propan-2-ol dihydrochloride Using 3.25 g of 4-acetoxy-2,5-dimethylphenol, 2.49 g of anhydrous potassium carbonate, 2.8 ml of chloromethyloxirane and 50 ml of methyl ethyl ketone, reaction and workup carried out as in Example 1-A gave about 2.97 g of 1-(4-acetoxy-2,5-dimethylphenoxy)-2,3-epoxypropane as yellow oil. Using the epoxy compound thus obtained, 2.66 g of 1-(2-methoxyphenyl)piperazine and 100 ml of dioxane, reaction and workup were carried out as in Examples 1-A and 4. After hydrolysis, workup and then conversion to hydrochloride with 2N HCl, recrystallization from methanol-acetone gave 0.80 g of white crystals, m.p. 214–215° C. (decomp.).

Elemental analysis: For $C_{22}H_{30}N_2O_4 \cdot 2HCl$ Calculated (%): C, 57.52; H, 7.02; N, 6.10; Found (%): C, 57.74; H, 7.21; N, 6.18.

EXAMPLE 22

1-(2,3-Dimethyl-4-hydroxyphenoxy)-3-[4-(2-methoxyphenyl)-1-piperazinyl]propan-2-ol hydrochloride Using 4.30 g of 4-acetoxy-2,3-dimethylphenol, 4.6 ml of chloromethyloxirane, 3.30 g of anhydrous potassium carbonate and 100 ml of methyl ethyl ketone, reaction and workup carried out as in Example 1-A gave about 6.05 g of 1-(4-acetoxy-2,3-dimethylphenoxy)-2,3-epoxypropane as brown oil. Using the epoxy compound thus obtained, 4.60 g of 1-(2-methoxyphenyl)piperazine and 100 ml of dioxane, reaction and workup were carried out as in Examples 1-A and 4. After hydrolysis and workup followed by conversion to hydrochloride with 2N HCl, recrystallization from methanol gave 2.55 g of white crystals, m.p. 228–230° C. (decomp.).

Elemental analysis: For $C_{22}H_{30}N_2O_4 \cdot HCl \cdot 1/2H_2O$ Calculated (%): C, 61.17; H, 7.47; N, 6.49; Found (%): C, 61.15; H, 7.26; N, 6.55.

EXAMPLE 23

1-(2,3,5-Trimethyl-4-hydroxyphenoxy)-3-[4-(2-methoxyphenyl)-1-piperazinyl]propan-2-ol Using 3.88 g of 1-(4-acetoxy-2,3,5-trimethylphenoxy)-2,3-epoxypropane, 3.58 g of 1-(2-methoxyphenyl)piperazine and 100 ml of dioxane, reaction and workup were carried out as in Examples 1-A and 4. After hydrolysis and workup, the residue obtained was recrystallized from benzene-hexane to give 2.06 g of white crystals, m.p. 163–165° C.

Elemental analysis: For $C_{23}H_{32}N_2O_4$ Calculated (%): C, 68.97; H, 8.05; N, 6.99; Found (%): C, 68.95; H, 7.67; N, 6.96.

EXAMPLE 24

1-(4-Benzyloxyphenoxy)-3-[4-(2,5-dimethoxyphenyl)-1-piperazinyl]propan-2-ol 2.56 g of 1-(4-benzyloxyphenoxy)-2,3-epoxypropane was dissolved in 100 ml of dioxane, and to this were added 2.95 g of 1-(2,5-dimethoxyphenyl)piperazine dihydrochloride and 3.5 ml of triethylamine and reaction and workup were carried out as in Example 1-A. The residue obtained was purified by column chromatography (silica gel, elution with ethyl acetate:hexane=1:1) to give 1.62 g of brown oil.

EXAMPLE 25

1-(4-Hydroxyphenoxy)-3-[4-(2,5-dimethoxyphenyl)-1-piperazinyl]propan-2-ol dihydrochloride Then, 1.62 g of the compound of Example 24 above was subjected to catalytic reduction with 5% palladium-carbon in 100 ml of dioxane and worked up as in Example 2. After conversion to hydrochloride with 2N HCl, recrystallization from methanol-acetone gave 1.27 g of white crystals, m.p. 205–207° C.

Elemental analysis: For $C_{21}H_{28}N_2O_5 \cdot 2HCl$ Calculated (%): C, 54.67; H, 6.55; N, 6.07; Found (%): C, 54.61; H, 6.47; N, 6.12.

EXAMPLE 26

1-(4-Benzyloxyphenoxy)-3-[4-(2,4-dimethoxyphenyl)-1-piperazinyl]propan-2-ol

Using 1.56 g of 1-(4-benzyloxyphenoxy)-2,3-epoxypropane, 1.80 g of 1-(2,4-dimethoxyphenyl)piperazine dihydrochloride, 1.9 ml of triethylamine and 50 ml of dioxane, reaction and workup were carried out as in Example 1-A. Purification by column chromatography (silica gel, elution with ethyl acetate:hexane =1:0.5) gave 1.96 g of pale red crystals, m.p. 110–112° C.

Elemental analysis: For $C_{28}H_{34}N_2O_5$ Calculated (%): C, 70.27; H, 7.16; N, 5.85; Found (%): C, 70.34; H, 7.17; N, 5.99.

EXAMPLE 27

1-(4-Hydroxyphenoxy)-3-[4-(2,4-dimethoxyphenyl)-1-piperazinyl]propan-2-ol dihydrochloride Then, 1.96 g of the compound of Example 26 was subjected to catalytic reduction with 5% palladium-carbon in 50 ml of dioxane and worked up as in Example 2. After conversion to hydrochloric acid with 2N HCl, recrystallization from methanol-acetone gave 1.47 g of white crystals, m.p. 213–215° C. (decomp.).

Elemental analysis: For $C_{21}H_{28}N_2O_5 \cdot 2HCl$ Calculated (%): C, 54.67; H, 6.55; N, 6.07; Found (%): C, 54.78; H, 6.66; N, 6.18.

EXAMPLE 28

1-(4-Benzyloxyphenoxy)-3-[4-(2-methoxy-5-methylphenyl)-1-piperazinyl]propan-2-ol Using 1.37 g of 1-(4-benzyloxyphenoxy)-2,3-epoxypropane, 50 ml of dioxane, 1.49 g of 1-(2-methoxy-5-methylphenyl)piperazine dihydrochloride and 1.6 ml of triethylamine, reaction and workup were carried out as in Example 1-A. Purification by column chromatography (silica gel, elution with ethyl acetate:hexane=1:1) gave 2.21 g of pale yellow oil.

EXAMPLE 29

1-(4-Hydroxyphenoxy)-3-[4-(2-methoxy-5-methylphenyl)-1-piperazinyl]propan-2-ol dihydrochloride Then, 2.21 g of the compound of Example 28 above was subjected to catalytic reduction with 5% palladium-carbon in 100 ml of dioxane and worked up as in Example 2. After conversion to hydrochloride with 2N HCl, recrystallization from methanol-acetone gave 1.65 g of white crystals, m.p. 222–224° C.

Elemental analysis: For $C_{21}H_{28}N_2O_4 \cdot 2HCl$ Calculated (%): C, 56.63; H, 6.79; N, 6.29; Found (%): C, 56.66; H, 6.85; N, 6.43.

EXAMPLE 30

1-(2-Methyl-4-hydroxyphenoxy)-3-[4-(2,5-dimethoxyphenyl)-1-piperazinyl]propan-2-ol dihydrochloride Using 2.5 g (0.02 mol) of methylhydroquinone and 2.8 g (0.02 mol) of benzoyl chloride, the procedure in Reference Example was followed. Recrystallization from ethanol-isopropyl ether gave 3.1 g of white crystals, m.p. 120–122° C. Then, using 2.3 g of the crystals, 1.4 g (0.01 mol) of anhydrous potassium carbonate, 4.6 g (0.05 mol) of chloromethyloxirane, 2.9 g (0.01 mol) of 1-(2,5-dimethoxyphenyl)piperazine dihydrochloride and 2.0 g (0.02 mol) of triethylamine, the procedures of Examples 3 and 4 were followed. Recrystallization from ethanol-isopropyl ether gave 1.0 g of white crystals, m.p. 168–170° C. (decomp.).

Elemental analysis: For $C_{22}H_{30}N_2O_5 \cdot 2HCl$ Calculated (%): C, 55.58; H, 6.78; N, 5.89; Found (%): C, 55.88; H, 7.07; N, 5.67.

EXAMPLE 31

1-(2-Methyl-4-hydroxyphenoxy)-3-[4-(2-methoxyphenyl)-1-piperazinyl]propan-2-ol dihydrochloride Using 2.5 g of methylhydroquinone and 2.8 g of benzoyl chloride, the procedure in Reference Example was followed. Recrystallization from ethanol-isopropyl ether gave 3.1 g of 4-benzoyloxy-2-methylphenol as white crystals, m.p. 120–122° C. Then, using 2.3 g of the crystals, 1.4 g of anhydrous potassium carbonate, 4.6 g of chloromethyloxirane and 1.9 g of 1-(2-methoxyphenyl)piperazine, the procedures of Examples 3 and 4 were followed to give 3.2 g of white crystals, m.p. 192–194° C. (decomp.).

Elemental analysis: For $C_{21}H_{28}N_2O_4 \cdot 2HCl \cdot 1/4 H_2O$ Calculated (%): C, 56.07; H, 6.83; N, 6.23; Found (%): C, 56.10; H, 6.82; N, 6.20.

EXAMPLE 32

1-(3-Methyl-4-hydroxyphenoxy)-3-[4-(2-methoxyphenyl)-1-piperazinyl]propan-2-ol dihydrochloride Using 5.0 g of methylhydroquinone and 5.6 g of benzoyl chloride, the procedure of Reference Example was followed. Recrystallization from ethanol-isopropyl ether gave 6.2 g of 4-benzoyloxy-2-methylphenol as white crystals, m.p. 120–122. Then, using 6.2 g of thus obtained white crystals, 5.1 g of benzyl bromide and 4.1 g of anhydrous potassium carbonate, the procedure of Reference Example was followed to give 7.6 g of 1-benzyloxy-2-methyl-4-benzoyloxybenzene as white crystals, m.p. 118–119° C. Then, using 7.6 g of thus obtained white crystals, 15 ml of 2N NaOH and 100 ml of methanol, the procedure of Reference Example was followed to give 3.8 g of 4-benzyloxy-3-methylphenol as white crystals, m.p. 70–71° C. Then, using 2.1 g of thus obtained white crystals, 1.4 g of anhydrous potassium carbonate, 4.6 g of chloromethyloxirane and 1.9 g of 1-(2-methoxyphenyl)piperazine, the procedures of Examples 1-A and 2 were followed. Recrystallization from methanol-ethyl acetate gave 3.0 g of white crystals, m.p. 214–216° C. (decomp.).

Elemental analysis: For $C_{21}H_{28}N_2O_4 \cdot 2HCl \cdot H_2O$ Calculated (%): C, 54.43; H, 6.96; N, 6.05; Found (%): C, 54.50; H, 7.04; N. 6.27.

EXAMPLE 33

1-(3-Methyl-4-benzyloxynaphthoxy)-3-[4-(2-pyridyl)-1-piperazinyl]propan-2-ol dihydrochloride Using 4.5 g of 4-benzyloxy-3-methylnaphthol, 8.4 g of chloromethyloxirane and 2.3 g of anhydrous potassium carbonate, the procedure of Example 1-A was followed. Recrystallization from methanol gave white crystals, m.p. 233–234° C. (decomp.).

Elemental analysis: For $C_{30}H_{33}N_2O_3 \cdot 2HCl \cdot 1/2H_2O$ Calculated (%): C, 64.23; H, 6.38; N, 7.49; Found (%): C, 64.26; H, 6.30; N, 7.58.

EXAMPLE 34

1-(3-Methyl-4-hydroxynaphthoxy)-3-[4-(2-pyridyl)-1-piperazinyl]propan-2-ol dihydrochloride Using 3.0 g of the compound of Example 33, the procedure of Example 2 was followed. Recrystallization from methanol-ethanol gave 1.5 g of white crystals, m.p. 260–262° C. (decomp.).

Elemental analysis: For $C_{23}H_{27}N_3O_3 \cdot 2HCl \cdot 1/2H_2O$ Calculated (%): C, 58.11; H, 6.36; N, 8.84; Found (%): C, 57.87; H, 6.60; N, 8.84.

EXAMPLE 35

1-(2-Methyl-4-benzoyloxynaphthoxy)-3-[4-(2-pyridyl)-1-piperazinyl]propan-2-ol dihydrochloride Using 10.3 g of 4-benzoyloxy-2-methylnaphthol, 19.2 g of chloromethyloxirane and 5.3 g of anhydrous potassium carbonate, the procedure of Example 3 was followed. Recrystallization from methanol-ethanol gave 4.6 g of white crystals, m.p. 268–270° C. (decomp.).

Elemental analysis: For $C_{30}H_{31}N_3O_4 \cdot 2HCl \cdot H_2O$ Calculated (%): C, 61.25; H, 5.99; N, 7.14; Found (%): C, 61.52; H, 5.92; N, 7.14.

EXAMPLE 36

1-(2-Methyl-4-hydroxynaphthoxy)-3-[4-(2-pyridyl)-1-piperazinyl]propan-2-ol dihydrochloride Using 2.9 g of the compound of Example 35, the procedure of Example 4 was followed to give 0.5 g of white crystals, m.p. 278–280° C. (decomp.).

Elemental analysis: For $C_{23}H_{27}N_3O_3 \cdot 2HCl \cdot H_2O$ Calculated (%): C, 57.03; H, 6.45; N, 8.67; Found (%): C, 57.06; H, 6.42; N, 8.62.

EXAMPLE 37

1-(2-Methyl-4-benzoyloxynaphthoxy)-3-[4-(2-pyrimidyl)-1-piperazinyl]propan-2-ol hydrochloride Using 9.0 g of 4-benzoyloxy-2-methylnaphthol, 16.8 g of chloromethyloxirane and 4.5 g of anhydrous potassium carbonate, the procedure of Example 3 was followed. Recrystallization from methanol-ethanol gave 3.9 g of white crystals, m.p. 230–232° C. (decomp.).

Elemental analysis: For $C_{29}H_{30}N_4O_4 \cdot 2HCl \cdot H_2O$ Calculated (%): C, 59.07; H, 5.81; N, 9.50; Found (%): C, 58.97; H, 5.82; N, 9.51.

EXAMPLE 38

1-(2-Methyl-4-hydroxynaphthoxy)-3-[4-(2-pyrimidyl)-1-piperazinyl]propan-2-ol dihydrochloride Using 2.9 g of the compound of Example 37, the procedure of Example 4 was followed to give 0.9 g of white crystals, m.p. 245–247° C. (decomp.).

Elemental analysis: For $C_{22}H_{26}N_4O_3 \cdot 2HCl \cdot H_2O$ Calculated (%): C, 54.44; H, 6.23; N, 11.54; Found (%): C, 54.48; H, 6.37; N, 11.31.

EXAMPLE 39

Intraocular Pressure Lowering Effect of the Present Compound

The present compound was tested for its intraocular pressure lowering effect.

[Tested Compounds]

The compounds of Examples 2, 4, 17, 20, 23, 25

[Experimental Animals]

Male Dutch rabbits of about 2.5 kg body weight were used in the test.

[Test method]

Intraocular pressure was measured by means of a contact type tonometer (ALCON Applanation Pneumatonograph) after instillation of oxybuprocaine hydrochloride [Anelocal (registered trademark) eye drops: SENJU Pharmaceutical Co., Ltd.] into both eyes of the rabbits for local anesthesia.

Eye drops were prepared each containing one of the test compounds at a concentration of 0.5% and 50 μl of it was instilled into the right eye. Intraocular pressure of both eyes was measured over time (0, 1, 2, 3, 4 hours). For analysis, Student t-test was conducted for the intraocular pressure measured at each time against the initial value.

[Test Results]

The results are shown in Table 1.

TABLE 1

| | Effect of the Present Compound on Intraocular Pressure of Rabbit | | | | |
|---|---|---|---|---|---|
| Tested Compound | 0 | 1 | 2 | 3 | 4 (hr) |
| Compound of Example 2 | 25.2 ± 1.30 | 21.8 ± 2.05[*1] | 24.4 ± 1.82 | 25.8 ± 2.39 | 26.6 ± 2.88 |
| Compound of Example 4 | 26.5 ± 1.75 | 17.3 ± 2.06[*3] | 15.0 ± 3.74[*2] | 15.8 ± 2.06[*3] | 20.8 ± 2.22[*2] |
| Compound of Example 17 | 30.0 ± 3.08 | 25.4 ± 2.79[*1] | 25.4 ± 2.88[*1] | 27.0 ± 3.08 | 28.6 ± 4.22 |
| Compound of Example 20 | 28.0 ± 3.81 | 22.2 ± 2.59[*1] | 25.2 ± 0.84 | 25.8 ± 2.59 | 28.0 ± 1.73 |
| Compound of Example 23 | 27.5 ± 3.42 | 20.8 ± 3.30[*1] | 22.8 ± 3.40 | 22.5 ± 3.42 | 23.8 ± 3.30 |
| Compound of Example 25 | 31.6 ± 2.41 | 26.8 ± 1.92[*2] | 25.4 ± 1.82[*2] | 28.6 ± 6.11 | 29.6 ± 2.07 |

Figures indicate mean ± SD (n = 4–5) in mmHg.
Significant difference from initial (0 hr)
[*1] $p < 0.05$.
[*2] $p < 0.01$.
[*3] $p < 0.001$.

As shown in Table 1, the tested compounds of the Examples significantly lowered the intraocular pressure one hour after instillation. In particular, with the compound of Example 4, a potent intraocular pressure lowering effect was observed since one hour after instillation, and the effect was found long lasting with its peak 2 hours after instillation. These results revealed the usefulness of the present compound as an intraocular pressure lowering agent.

EXAMPLE 40

Effect of the Present Compound on Blood Pressure of SHR Rat

The present compound was tested for its blood pressure lowering effect.

[Test Compounds]

The compounds of Examples 2, 4, 17, 20, 22, 23

[Experimental Animals]

About 25-week old male SHR/Izm rats were used in the test.

[Test Method]

Initial value of the blood pressure of rat tail vein was measured with a non-invasive automatic manometer for small animals, UR-5000 (UEDA Seisakusho), and then one of the test compounds 30 mg/kg was orally administered. Blood pressure was measured in the same manner 1, 2, 3 and 4 hours after administration. For analysis, Student t-test was conducted for the blood pressure measured at each time against the initial value.

[Results]

The results are shown in Table 2.

TABLE 2

Effect of the present Compound on Blood Pressure of SHR Rat

| Tested Compound | 0 | 1 | 2 | 3 | 4 (hr) |
|---|---|---|---|---|---|
| Compound of Example 2 | 216.8 ± 18.0 | 204.0 ± 17.6 | 192.2 ± 6.2[*1] | 191.2 ± 14.6[*1] | 187.8 ± 11.4[*1] |
| Compound of Example 4 | 240.0 ± 8.5 | 201.8 ± 7.7[*3] | 207.8 ± 13.8[*2] | 212.2 ± 3.8[*3] | 212.2 ± 20.8[*1] |
| Compound of Example 17 | 247.3 ± 23.2 | 214.8 ± 9.9[*1] | 230.8 ± 13.0 | 225.0 ± 13.0 | 219.5 ± 10.6 |
| Compound of Example 20 | 250.3 ± 14.3 | 204.8 ± 16.9[*2] | 215.0 ± 11.0[*2] | 217.5 ± 15.2[*1] | 216.3 ± 18.0[*1] |
| Compound of Example 22 | 247.0 ± 10.7 | 218.3 ± 11.3[*1] | 231.0 ± 14.5 | 236.5 ± 9.1 | 241.0 ± 9.8 |
| Compound of Example 23 | 204.0 ± 14.4 | 193.3 ± 15.4 | 192.0 ± 10.8 | 179.3 ± 7.8[*1] | 192.0 ± 15.1 |

Figures indicate mean ± SD (n = 4–5) in mmHg.
Significant difference from initial (0 hr)
[*1] $p < 0.05$.
[*2] $p < 0.01$.
[*3] $p < 0.001$.

As shown in Table 2, with each of the tested compounds of Examples, blood pressure began to lower one hour after administration, and a significant blood pressure lowering effect was observed with each of the compounds. These results revealed that the present compound is useful as an antihypertensive agent.

EXAMPLE 41

Radical Scavenging Ability of the Present Compound

The present compound was tested for its scavenging ability on a stable radical of 1,1-diphenyl-2-picrylhydrazide (DPPH).

[Test Compound]

| The compound of Example 2 | $10^{-6}$–$10^{-3}$ M |
|---|---|
| The compound of Example 4 | $10^{-6}$–$10^{-3}$ M |

[Test Method]

The test was carried out according to the method described by Blois, M. S., Nature, 181: 1199 (1995).

Each of the test compound was dissolved in purified water to prepare $10^{-5}$–$10^{-2}$ M test solutions. To 300 μl each of the test solutions was added 2.7 ml of a 0.011 Mn solution of the stable radical, DPPH, in ethanol and stirred. The mixture was allowed to stand for 20 minutes, and absorbance at 517 nm was measured. Radical scavenging ability was determined for each of the test solutions according to the following equation.

Radical scavenging rate (%)=(Absorbance of control−Absorbance of test solution×Absorbance of control)×100

[Test Results]

TABLE 3

Radical Scavenging Ability of the Present Compound

| Test compound | Final Concentration (μM) | Radical scavenging rate (%) |
|---|---|---|
| Compound of Example 2 | 1000 | 99.8 |
|  | 100 | 99.4 |
|  | 30 | 61.0 |
|  | 10 | 24.9 |
|  | 1 | 7.8 |
| Compound of Example 4 | 1000 | 91.7 |
|  | 100 | 75.4 |
|  | 30 | 37.7 |
|  | 10 | 16.6 |
|  | 1 | 6.7 |

As shown in Table 3, the compounds of Examples 2 and 4 concentration-dependently exhibited a radical scavenging activity. $IC_{50}$ for the compounds was 23 and 42 μM, respectively. These results revealed that the present compound is useful as a radical scavenging agent.

EXAMPLE 42

Oral Tablet

| Compound of Example 4 | 30 mg |
|---|---|
| Lactose | 80 mg |
| Potato starch | 17 mg |
| Polyethylene glycol 6000 | 3 mg |

A tablet is formed by a conventional method using the above ingredients as the materials for one tablet.

EXAMPLE 43

Eye Drops

| Compound of Example 4 (hydrochloride) | 0.3 g |
|---|---|
| Glycerol | 2.5 g |
| Benzalkonium chloride | 0.005 g |
| Sodium acetate | q.s. |
| Sterile purified water | To 100 ml |
|  | pH 4.5 |

An eye drops is prepared by admixing the above ingredients and then sterilizing by filtration.

EXAMPLE 44

Eye Drops

| | |
|---|---|
| Compound of Example 23 | 0.3 g |
| Boric acid | 1.8 g |
| Sodium acetate | 0.2 g |
| Benzalkonium chloride | 0.005 g |
| Hydrochloric acid | q.s. |
| Sterile purified water | To 100 ml |
| | pH 5.0 |

An eye drops is prepared by admixing the above ingredients and then sterilizing by filtration.

INDUSTRIAL APPLICABILITY

The hydroquinone derivative of the present invention can be used advantageously an antihypertensive, intraocular pressure lowering and radical scavenging agent.

What is claimed is:

1. A hydroquinone compound represented by the following formula

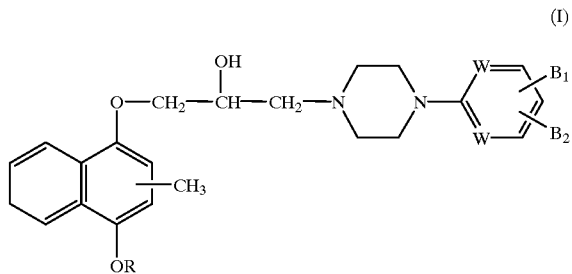

(I)

wherein
$B_1$ and $B_2$ in formula (I) are the same and are at any position on the benzene ring (when W is nitrogen, however, at any other position on the benzene ring) and each denotes halogen, or lower alkoxy,
the substituent $CH_3$ is at position 2 or 3,
Ws are the same or different and each denotes a nitrogen or carbon atom,
R denotes hydrogen, acetyl, benzoyl, or benzyl,
or a pharmacologically acceptable salt thereof.

2. A hydroquinone compound which is 1-(2-methyl-4-hydroxynaphthoxy)-3-[4-(2-methylphenyl)-1-piperazinyl]propan-2-ol, or a pharmacologically acceptable salt thereof.

3. A hydroquinone compound which is 1-(3-methyl-4-benzyloxynaphthoxy)-3-[4-(2-fluorophenyl)-1-piperazinyl]propan-2-ol, or a pharmacologically acceptable salt thereof.

4. A hydroquinone compound which is 1-(3-methyl-4-hydroxynaphthoxy)-3-[4-(2-fluorophenyl)-1-piperazinyl]propan-2-ol, or a pharmacologically acceptable salt thereof.

5. A hydroquinone compound which is 1-(2-methyl-4-hydroxynaphthoxy)-3-[4-(2,5-dimethoxyphenyl)-1-piperazinyl]propan-2-ol, or a pharmacologically acceptable salt thereof.

6. A hydroquinone compound which is 1-(2-methyl-4-hydroxynaphthoxy)-3-[4-(3,4-dimethoxyphenyl)-1-piperazinyl]propan-2-ol, or a pharmacologically acceptable salt thereof.

7. A hydroquinone compound which is 1-(2-methyl-4-hydroxynaphthoxy)-3-[4-(2,4-dimethoxyphenyl)-1-piperazinyl]propan-2-ol, or a pharmacologically acceptable salt thereof.

8. A hydroquinone compound which is 1-(4-benzyloxy-2,3-dimethoxy-5-methylphenoxy)-3-[4-(2-methoxyphenyl)-1-piperazinyl]propan-2-ol, or a pharmacologically acceptable salt thereof.

9. A hydroquinone compound which is 1-(2,3-dimethoxy4-hydroxy-5-methylphenoxy)-1-[4-(2-methyloxyphenyl)-1-piperazinyl]propan-2-ol, or a pharmacologically acceptable salt thereof.

10. A hydroquinone compound which is 1-(4-benzyloxy-3,5-dimethylphenoxy)-3-[4-(2-methoxyphenyl)-1-piperazinyl]propan-2-ol, or a pharmacologically acceptable salt thereof.

11. A hydroquinone compound which is 1-(3,5-dimethyl-4-hydroxyphenoxy)-3-[4-(2-methoxyphenyl)-1-piperazinyl]propan-2-ol, or a pharmacologically acceptable salt thereof.

12. A hydroquinone compound which is 1-(4-benzyloxy-3-tert-butylphenoxy)-3-[4-(2-methoxyphenyl)-1-piperazinyl]propan-2-ol, or a pharmacologically acceptable salt thereof.

13. A hydroquinone compound which is 1-(3-tert-butyl)-4-hydroxyphenoxy)-3-[4-(2-methoxyphenyl)-1-piperazinyl]propan-2-ol, or a pharmacologically acceptable salt thereof.

14. A hydroquinone compound which is 1-(2,5-dimethyl-4-hydroxyphenoxy)-3-[4-(2-methoxyphenyl)-1-piperazinyl]propan-2-ol, or a pharmacologically acceptable salt thereof.

15. A hydroquinone compound which is 1-(2,3-dimethyl-4-hydroxyphenoxy)-3-[4-(2-methoxyphenyl)-1-piperazinyl]propan-2-ol, or a pharmacologically acceptable salt thereof.

16. A hydroquinone compound which is 1-(2,3,5-trimethyl-4-hydroxyphenoxy)-3-[4-(2-methoxyphenyl)-1-piperazinyl]propan-2-ol, or a pharmacologically acceptable salt thereof.

17. A hydroquinone compound which is 1-(4-benzyloxyphenoxy)-3-[4-(2,5-dimethoxyphenyl)-1-piperazinyl]propan-2-ol, or a pharmacologically acceptable salt thereof.

18. A hydroquinone compound which is 1-(4-benzyloxyphenoxy)-3-[4-(2,4-dimethoxyphenyl)-1-piperazinyl]propan-2-ol, or a pharmacologically acceptable salt thereof.

19. A hydroquinone compound which is 1-(3-methyl-4-hydroxynaphthoxy)-3-[4-(2-pyridyl)-1-piperazinyl]propan-2-ol, or a pharmacologically acceptable salt thereof.

20. A hydroquinone compound which is 1-(3-methyl-4-hydroxynaphthoxy)-3-[4-(2-pyridyl)-1-piperazinyl]propan-2-ol, or a pharmacologically acceptable salt thereof.

21. A hydroquinone compound which is 1-(2-methyl-4-benzoylnaphthoxy)-3-[4-(2-pyridyl)-1-piperazinyl]propan-2-ol, or a pharmacologically acceptable salt thereof.

22. A hydroquinone compound which is 1-(2-methyl-4-hydroxynaphthoxy)-3-[4-(2-pyridyl)-1-piperazinyl]propan-2-ol, or a pharmacologically acceptable salt thereof.

23. A hydroquinone compound which is 1-(2-methyl-4-benzoyloxynaphthoxy)-3-[4-(2-pyrimidyl)-1-piperazinyl]propan-2-ol, or a pharmacologically acceptable salt thereof.

24. The hydroquinone compound of claim 1 which is 1-(2-methyl-4-hydroxynaphthoxy)-3-[4-(2-pyrimidyl)-1-piperazinyl]propan-2-ol, or a pharmacologically acceptable salt thereof.

25. An intraocular pressure lowering pharmaceutical composition comprising a hydroquinone compound represented by the following formula:

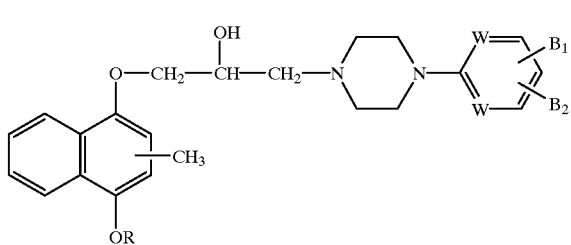

(I)

wherein
  $B_1$ and $B_2$ in formula (I) are the same and are at any position on the benzene ring (when W is nitrogen, however, at any other position on the benzene ring) and each denotes halogen or lower alkoxy,
  the substituent $CH_3$ is at position 2 or 3,
  Ws are the same or different and each denotes a nitrogen or carbon atom,
  R denotes hydrogen,
or a pharmaceutically acceptable salt thereof.

26. An antihypertensive pharmaceutical composition comprising a hydroquinone compound represented by the following formula:

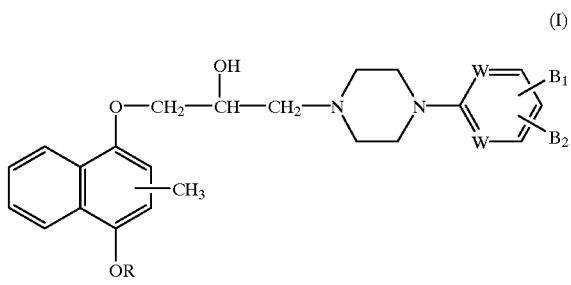

(I)

wherein
  $B_1$ and $B_2$ in formula (I) are the same and are at any position on the benzene ring (when W is nitrogen, however, at any other position on the benzene ring) and each denotes halogen or lower alkoxy,
  the substituent $CH_3$ is at position 2 or 3,
  Ws are the same or different and each denotes a nitrogen or carbon atom,
  R denotes hydrogen,
or a pharmaceutically acceptable salt thereof.

27. A radical scavenging composition comprising a hydroquinone compound represented by the following formula:

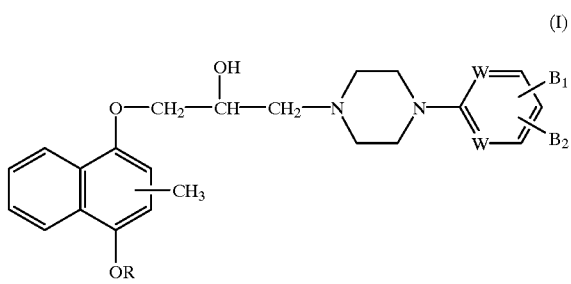

(I)

wherein
  $B_1$ and $B_2$ in formula (I) are the same and are at any position on the benzene ring (when W is nitrogen, however, at any other position on the benzene ring) and each denotes halogen or lower alkoxy,
  the substituent $CH_3$ is at position 2 or 3,
  Ws are the same or different and each denotes a nitrogen or carbon atom,
  R denotes hydrogen,
or pharmaceutically acceptable salt thereof.

28. An intraocular pressure lowering pharmaceutical composition comprising a hydroquinone compound of:

1-(2-methyl-4-hydroxynaphthoxy)-3-[4-(2-methylphenyl)-1-piperazinyl]propan-2-ol;
1-(3-methyl-4-hydroxynaphthoxy)-3-[4-(2-fluorophenyl)-1-piperazinyl]propan-2-ol;
1-(2-methyl-4-hydroxynaphthoxy)-3-[4-(2,5-dimethoxyphenyl)-1-piperazinyl]propan-2-ol;
1-(2-methyl-4-hydroxynaphthoxy)-3-[4-(3,4-dimethoxyphenyl)-1-piperazinyl]propan-2-ol;
1-(2-methyl-4-hydroxynaphthoxy)-3-[4-(2,4-dimethoxyphenyl)-1-piperazinyl]propan-2-ol;
1-(2,3-dimethoxy-4-hydroxy-5-methylphenoxy)-1-[4-(2-methoxyphenyl)-1-piperazinyl]propan-2-ol;
1-(3,5-dimethyl-4-hydroxyphenoxy)-3-[4-(2-methoxyphenyl)-1-piperazinyl]propan-2-ol;
1-(3-tert-butyl-4-hydroxyphenoxy)-3-[4-(2-methoxyphenyl)-1-piperazinyl]propan-2-ol;
1-(2,5-dimethyl-4-hydroxyphenoxy)-3-[4-(2-methoxyphenyl)-1-piperazinyl]propan-2-ol;
1-(2,3-dimethyl-4-hydroxyphenoxy)-3-[4-(2-methoxyphenyl)-1-piperazinyl]propan-2-ol;
1-(2,3,5-trimethyl-4-hydroxyphenoxy)-3-[4-(2-methoxyphenyl)-1-piperazinyl]propan-2-ol;
1-(3-methyl-4-hydroxynaphthoxy)-3-[4-(2-pyridyl)-1-piperazinyl]propan-2-ol;
1-(2-methyl-4-hydroxynaphthoxy)-3-[4-(2-pyridyl)-1-piperazinyl]propan-2-ol;
1-(2-methyl-4-hydroxynaphthoxy)-3-[4-(2-pyrimidyl)-1-piperazinyl]propan-2-ol;

or a pharmaceutically acceptable salt thereof.

29. An antihypertensive pharmaceutical composition comprising a hydroquinone compound of:

1-(2-methyl-4-hydroxynaphthoxy)-3-[4-(2-methylphenyl)-1-piperazinyl]propan-2-ol;
1-(3-methyl-4-hydroxynaphthoxy)-3-[4-(2-fluorophenyl)-1-piperazinyl]propan-2-ol;
1-(2-methyl-4-hydroxynaphthoxy)-3-[4-(2,5-dimethoxyphenyl)-1-piperazinyl]propan-2-ol;
1-(2-methyl-4-hydroxynaphthoxy)-3-[4-(3,4-dimethoxyphenyl)-1-piperazinyl]propan-2-ol;
1-(2-methyl-4-hydroxynaphthoxy)-3-[4-(2,4-dimethoxyphenyl)-1-piperazinyl]propan-2-ol;
1-(2,3-dimethoxy-4-hydroxy-5-methylphenoxy)-1-[4-(2-methoxyphenyl)-1-piperazinyl]propan-2-ol;
1-(3,5-dimethyl-4-hydroxyphenoxy)-3-[4-(2-methoxyphenyl)-1-piperazinyl]propan-2-ol;
1-(3-tert-butyl-4-hydroxyphenoxy)-3-[4-(2-methoxyphenyl)-1-piperazinyl]propan-2-ol;
1-(2,5-dimethyl-4-hydroxyphenoxy)-3-[4-(2-methoxyphenyl)-1-piperazinyl]propan-2-ol;
1-(2,3-dimethyl-4-hydroxyphenoxy)-3-[4-(2-methoxyphenyl)-1-piperazinyl]propan-2-ol;
1-(2,3,5-trimethyl-4-hydroxyphenoxy)-3-[4-(2-methoxyphenyl)-1-piperazinyl]propan-2-ol;
1-(3-methyl-4-hydroxynaphthoxy)-3-[4-(2-pyridyl)-1-piperazinyl]propan-2-ol;

1-(2-methyl-4-hydroxynaphthoxy)-3-[4-(2-pyridyl)-1-piperazinyl]propan-2-ol;
1-(2-methyl-4-hydroxynaphthoxy)-3-[4-(2-pyrimidyl)-1-piperazinyl]propan-2-ol;

or a pharmaceutically acceptable salt thereof.

30. A radical scavenging composition comprising a hydroquinone compound of:

1-(2-methyl-4-hydroxynaphthoxy)-3-[4-(2-methylphenyl)-1-piperazinyl]propan-2-ol;
1-(3-methyl-4-hydroxynaphthoxy)-3-[4-(2-fluorophenyl)-1-piperazinyl]propan-2-ol;
1-(2-methyl-4-hydroxynaphthoxy)-3-[4-(2,5-dimethoxyphenyl)-1-piperazinyl]propan-2-ol;
1-(2-methyl-4-hydroxynaphthoxy)-3-[4-(3,4-dimethoxyphenyl)-1-piperazinyl]propan-2-ol;
1-(2-methyl-4-hydroxynaphthoxy)-3-[4-(2,4-dimethoxyphenyl)-1-piperazinyl]propan-2-ol;
1-(2,3-dimethoxy-4-hydroxy-5-methylphenoxy)-1-[4-(2-methoxyphenyl)-1-piperazinyl]propan-2-ol;
1-(3,5-dimethyl-4-hydroxyphenoxy)-3-[4-(2-methoxyphenyl)-1-piperazinyl]propan-2-ol;
1-(3-tert-butyl-4-hydroxyphenoxy)-3-[4-(2-methoxyphenyl)-1-piperazinyl]propan-2-ol;
1-(2,5-dimethyl-4-hydroxyphenoxy)-3-[4-(2-methoxyphenyl)-1-piperazinyl]propan-2-ol;
1-(2,3-dimethyl-4-hydroxyphenoxy)-3-[4-(2-methoxyphenyl)-1-piperazinyl]propan-2-ol;
1-(2,3,5-trimethyl-4-hydroxyphenoxy)-3-[4-(2-methoxyphenyl)-1-piperazinyl]propan-2-ol;
1-(3-methyl-4-hydroxynaphthoxy)-3-[4-(2-pyridyl)-1-piperazinyl]propan-2-ol;
1-(2-methyl-4-hydroxynaphthoxy)-3-[4-(2-pyridyl)-1-piperazinyl]propan-2-ol;
1-(2-methyl-4-hydroxynaphthoxy)-3-[4-(2-pyrimidyl)-1-piperazinyl]propan-2-ol;

or a pharmaceutically acceptable salt thereof.

31. A method for lowering intraocular pressure in a human comprising administering to said human an effective amount of a hydroquinone compound represented by the following formula:

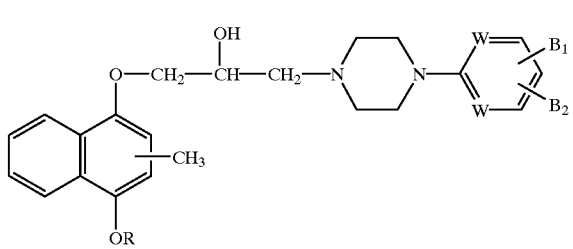

(I)

wherein
$B_1$ and $B_2$ in formula (I) are the same or different and are at any position on the benzene ring (when W is nitrogen, however, at any other position on the benzene ring) and each denotes halogen, hydroxyl, or lower alkoxy,
the substituent $CH_3$ is at position 2 or 3,
Ws are the same or different and each denotes a nitrogen or carbon atom,
R denotes hydrogen,
or a pharmaceutically acceptable salt thereof.

32. A method for lowering blood pressure of a human with hypertension comprising administering to said human an effective amount of a hydroquinone compound represented by the following formula:

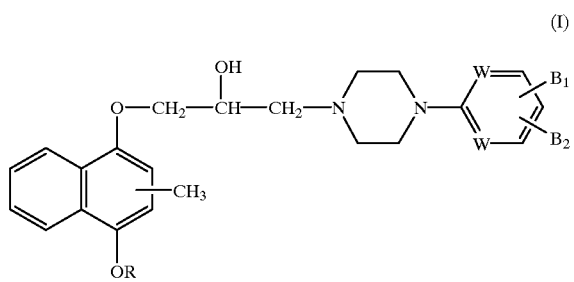

(I)

wherein
$B_1$ and $B_2$ in formula (I) are the same and are at any position on the benzene ring (when W is nitrogen, however, at any other position on the benzene ring) and each denotes halogen or lower alkoxy,
the substituent $CH_3$ is at position 2 or 3,
Ws are the same or different and each denotes a nitrogen or carbon atom,
R denotes hydrogen,
or a pharmaceutically acceptable salt thereof.

33. A method for radical scavenging a cosmetic composition or a foodstuff comprising adding to said cosmetic composition or foodstuff an effective amount of a hydroquinone compound represented by the following formula:

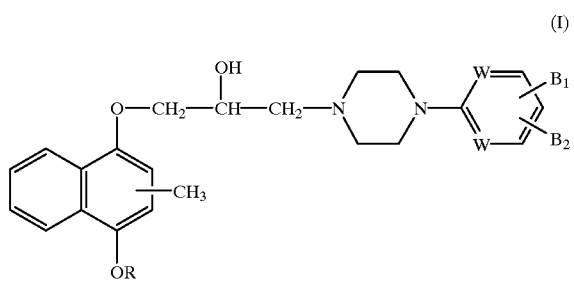

(I)

wherein
$B_1$ and $B_2$ in formula (I) are the same or different and are at any position on the benzene ring (when W is nitrogen, however, at any other position on the benzene ring) and each denotes halogen, hydroxyl, or lower alkoxy,
the substituent $CH_3$ is at position 2 or 3,
Ws are the same or different and each denotes a nitrogen or carbon atom,
R denotes hydrogen,
or a pharmaceutically acceptable salt thereof.

34. A method for lowering intraocular pressure in a human comprising administering to said human an effective amount of a hydroquinone compound of:

1-(2-methyl-4-hydroxynaphthoxy)-3-[4-(2-methylphenyl)-1-piperazinyl]propan-2-ol;
1-(3-methyl-4-hydroxynaphthoxy)-3-[4-(2-fluorophenyl)-1-piperazinyl]propan-2-ol;
1-(2-methyl-4-hydroxynaphthoxy)-3-[4-(2,5-dimethoxyphenyl)-1-piperazinyl]propan-2-ol;
1-(2-methyl-4-hydroxynaphthoxy)-3-[4-(3,4-dimethoxyphenyl)-1-piperazinyl]propan-2-ol;

1-(2-methyl-4-hydroxynaphthoxy)-3-[4-(2,4-dimethoxyphenyl)-1-piperazinyl]propan-2-ol;

1-(2-methyl-4-hydroxynaphthoxy)-3-[4-(2-hydroxyphenyl)-1-piperazinyl]propan-2-ol;

1-(2,3-dimethoxy-4-hydroxy-5-methylphenoxy)-1-[4-(2-methoxyphenyl)-1-piperazinyl]propan-2-ol;

1-(3,5-dimethyl-4-hydroxyphenoxy)-3-[4-(2-methoxyphenyl)-1-piperazinyl]propan-2-ol;

1-(3-tert-butyl)-4-hydroxyphenoxy)-3-[4-(2-methoxyphenyl)-1-piperazinyl]propan-2-ol;

1-(2,5-dimethyl-4-hydroxyphenoxy)-3-[4-(2-methoxyphenyl)-1-piperazinyl]propan-2-ol;

1-(2,3-dimethyl-4-hydroxyphenoxy)-3-[4-(2-methoxyphenyl)-1-piperazinyl]propan-2-ol;

1-(2,3,5-trimethyl-4-hydroxyphenoxy)-3-[4-(2-methoxyphenyl)-1-piperazinyl]propan-2-ol;

1-(3-methyl-4-hydroxynaphthoxy)-3-[4-(2-pyridyl)-1-piperazinyl]propan-2-ol;

1-(2-methyl-4-hydroxynaphthoxy)-3-[4-(2-pyridyl)-1-piperazinyl]propan-2-ol; or 1-(2-methyl-4-hydroxynaphthoxy)-3-[4-(2-pyrimidyl)-1-piperazinyl]propan-2-ol;

or a pharmacologically acceptable salt thereof.

35. A method for lowering blood pressure of a human with hypertension comprising administering to said human an effective amount of a compound of:

1-(2-methyl-4-hydroxynaphthoxy)-3-[4-(2-methylphenyl)-1-piperazinyl]propan-2-ol;

1-(3-methyl-4-hydroxynaphthoxy)-3-[4-(2-fluorophenyl)-1-piperazinyl]propan-2-ol;

1-(2-methyl-4-hydroxynaphthoxy)-3-[4-(2,5-dimethoxyphenyl)-1-piperazinyl]propan-2-ol;

1-(2-methyl-4-hydroxynaphthoxy)-3-[4-(3,4-dimethoxyphenyl)-1-piperazinyl]propan-2-ol;

1-(2-methyl-4-hydroxynaphthoxy)-3-[4-(2,4-dimethoxyphenyl)-1-piperazinyl]propan-2-ol;

1-(2,3-dimethoxy-4-hydroxy-5-methylphenoxy)-1-[4-(2-methoxyphenyl)-1-piperazinyl]propan-2-ol;

1-(3,5-dimethyl-4-hydroxyphenoxy)-3-[4-(2-methoxyphenyl)-1-piperazinyl]propan-2-ol;

1-(3-tert-butyl)-4-hydroxyphenoxy)-3-[4-(2-methoxyphenyl)-1-piperazinyl]propan-2-ol;

1-(2,5-dimethyl-4-hydroxyphenoxy)-3-[4-(2-methoxyphenyl)-1-piperazinyl]propan-2-ol;

1-(2,3-dimethyl-4-hydroxyphenoxy)-3-[4-(2-methoxyphenyl)-1-piperazinyl]propan-2-ol;

1-(2,3,5-trimethyl-4-hydroxyphenoxy)-3-[4-(2-methoxyphenyl)-1-piperazinyl]propan-2-ol;

1-(3-methyl-4-hydroxynaphthoxy)-3-[4-(2-pyridyl)-1-piperazinyl]propan-2-ol;

1-(2-methyl-4-hydroxynaphthoxy)-3-[4-(2-pyridyl)-1-piperazinyl]propan-2-ol; or 1-(2-methyl-4-hydroxynaphthoxy)-3-[4-(2-pyrimidyl)-1-piperazinyl]propan-2-ol;

or a pharmacologically acceptable salt thereof.

36. A method for radical scavenging a cosmetic composition or a foodstuff comprising adding to said cosmetic composition or foodstuff an effective amount of a hydroquinone compound of:

1-(2-methyl-4-hydroxynaphthoxy)-3-[4-(2-methylphenyl)-1-piperazinyl]propan-2-ol;

1-(3-methyl-4-hydroxynaphthoxy)-3-[4-(2-fluorophenyl)-1-piperazinyl]propan-2-ol;

1-(2-methyl-4-hydroxynaphthoxy)-3-[4-(2,5-dimethoxyphenyl)-1-piperazinyl]propan-2-ol;

1-(2-methyl-4-hydroxynaphthoxy)-3-[4-(3,4-dimethoxyphenyl)-1-piperazinyl]propan-2-ol;

1-(2-methyl-4-hydroxynaphthoxy)-3-[4-(2,4-dimethoxyphenyl)-1-piperazinyl]propan-2-ol;

1-(2-methyl-4-hydroxynaphthoxy)-3-[4-(2-hydroxyphenyl)-1-piperazinyl]propan-2-ol;

1-(2,3-dimethoxy-4-hydroxy-5-methylphenoxy)-1-[4-(2-methoxyphenyl)-1-piperazinyl]propan-2-ol;

1-(3,5-dimethyl-4-hydroxyphenoxy)-3-[4-(2-methoxyphenyl)-1-piperazinyl]propan-2-ol;

1-(3-tert-butyl)-4-hydroxyphenoxy)-3-[4-(2-methoxyphenyl)-1-piperazinyl]propan-2-ol;

1-(2,5-dimethyl-4-hydroxyphenoxy)-3-[4-(2-methoxyphenyl)-1-piperazinyl]propan-2-ol;

1-(2,3-dimethyl-4-hydroxyphenoxy)-3-[4-(2-methoxyphenyl)-1-piperazinyl]propan-2-ol;

1-(2,3,5-trimethyl-4-hydroxyphenoxy)-3-[4-(2-methoxyphenyl)-1-piperazinyl]propan-2-ol;

1-(4-hydroxyphenoxy)-3-[4-(2,5-dimethoxyphenyl)-1-piperazinyl]propan-2-ol;

1-(4-hydroxyphenoxy)-3-[4-(2,4-dimethoxyphenyl)-1-piperazinyl]propan-2-ol;

1-(4-hydeoxyphenoxy)-3-[4-(2-methoxy-5-methylphenyl)-1-piperazinyl]propan-2-ol;

1-(2-methyl-4-hydroxyphenoxy)-3-[4-(2,5-dimethoxyphenyl)-1-piperazinyl]propan-2-ol;

1-(2-methyl-4-hydroxyphenoxy)-3-[4-(2-methoxyphenyl)-1-piperazinyl]propan-2-ol;

1-(3-methyl-4-hydroxyphenoxy)-3-[4-(2-methoxyphenyl)-1-piperazinyl]propan-2-ol;

1-(3-methyl-4-hydroxynaphthoxy)-3-[4-(2-pyridyl)-1-piperazinyl]propan-2-ol;

1-(2-methyl-4-hydroxynaphthoxy)-3-[4(2-pyrimidyl)-1-piperazinyl]propan-2-ol; or 1-(2-methyl-4-hydroxynaphthoxy)-3-[4-(2-pyrimidyl)-1-piperazinyl]propan-2-ol;

or a pharmacologically acceptable salt thereof.

\* \* \* \* \*